(12) United States Patent
Blanc-Brude et al.

(10) Patent No.: US 10,139,420 B2
(45) Date of Patent: Nov. 27, 2018

(54) METHODS FOR TREATING VASO-OCCLUSIVE CRISIS USING NON-MODIFIED ANNEXIN V

(75) Inventors: Olivier Blanc-Brude, Paris (FR); Pierre-Louis Tharaux, Paris (FR); Chantal Boulanger, Paris (FR); Sylvain Lejeune, Bobigny (FR); Francois Lionnet, Paris (FR)

(73) Assignees: ISNERM (Institut National de la Sante et de la Recherche Medicale), Paris (FR); Assistance Publique—Hopitaux de Paris, Paris (FR)

( * ) Notice: Subject to any disclaimer, the term of this patent is extended or adjusted under 35 U.S.C. 154(b) by 835 days.

(21) Appl. No.: 14/003,919

(22) PCT Filed: Mar. 9, 2012

(86) PCT No.: PCT/EP2012/054153
§ 371 (c)(1),
(2), (4) Date: Oct. 31, 2013

(87) PCT Pub. No.: WO2012/120130
PCT Pub. Date: Sep. 13, 2012

(65) Prior Publication Data
US 2014/0044735 A1    Feb. 13, 2014

(30) Foreign Application Priority Data

Mar. 9, 2011 (EP) ..................................... 11305250
Mar. 10, 2011 (EP) ..................................... 11305261

(51) Int. Cl.
*G01N 33/72* (2006.01)
(52) U.S. Cl.
CPC ....... *G01N 33/721* (2013.01); *G01N 2800/22* (2013.01); *G01N 2800/56* (2013.01)
(58) Field of Classification Search
None
See application file for complete search history.

(56) References Cited

U.S. PATENT DOCUMENTS 6,982,154 B2 * 1/2006 Allison .............. C07K 14/4721
424/178.1
2014/0044735 A1   2/2014 Blanc-Brude

FOREIGN PATENT DOCUMENTS

WO    2004/013303 A2    2/2004
WO    2012/120130 A1    9/2012

OTHER PUBLICATIONS

Shet et al., "Sickle blood contains tissue factor-positive microparticles derived from endothelial cells and monocytes", Blood, Oct. 1, 2003, pp. 2678-2683, vol. 102, No. 7, American Society of Hematology, US.
Simak et al., "Elevated circulating endothelial membrane microparticles in paroxysmal nocturnal haemoglobinuria", British Journal of Haematology, Jun. 1, 2004, pp. 804-813, vol. 125, No. 6, Wiley-Blackwell Publishing Ltd, GB.
Sabaa et al., "Endothelin receptor antagonism prevents hypoxia-induced mortality and morbidity in a mouse model of sickle-cell disease", Journal of Clinical Investigation, May 1, 2008, pp. 1924-1933, vol. 118, No. 5, American Society for Clinical Investigation, US.
Gayen et al., "Phosphatidylserine-positive erythrocytes bind to immobilized and soluble thrombospondin-1 via its heparin-binding domain", Translational Research, Oct. 1, 2008, pp. 1650177, vol. 152, No. 4, Elsevier, Amsterdam, NL.
De Franceschi, "Pathophisiology of sickle cell disease and new drugs for the treatment", Mediterranean Journal of Hematology and Infectious Diseases, Jan. 1, 2009, IT.
Van Tits et al., "Plasma annexin A5 and microparticle phosphatidylserine levels are elevated in sickle cell disease and increase further during painful crisis", Biochemical and Biophysical Communications, Dec. 4, 2009, pp. 161-164, vol. 390, No. 1, Elsevier, NL.
Wood et al., Increased Erythrocyte Phosphatidylserine Exposure in Sickle Cell Disease: Flow-Cytometric Measurement and Clinical Associations; Sep. 1, 1996 Blood, pp. 1873-1880 vol. 88, No. 5.
Setty et al., Role of Erythrocyte Phosphatidylserine in Sickle Red Cell-Endothelial Adhension; Mar. 1, 2002 Blood, pp. 1564-1571 vol. 99, No. 9.

* cited by examiner

*Primary Examiner* — Sharon X Wen
(74) *Attorney, Agent, or Firm* — W&C IP

(57) ABSTRACT

The present invention relates to methods for determining the risk of severe complications in hemolytic diseases. The present invention relates to a method for determining whether a patient suffering from sickle cell disease is at risk for a vaso-occlusive crisis comprising the steps consisting of i) determining the level of cell microparticles in a blood sample obtained from said patient and ii) determining the level of heme and/or hemoglobin contained in said cell microparticles. The present invention also relates to a method for a method the severe complication in hemolytic diseases comprising the steps consisting of i) determining the level of cell microparticles in a blood sample obtained from said patient and ii) determining the level of heme and/or hemoglobin contained in said cell microparticles. The present invention also relates to a method for preventing a vaso-occlusive crisis in a patient afflicted with by sickle cell disease comprising depleting the blood-borne microparticles laden in heme and hemoglobin from the blood of said patient.

Figure 1:
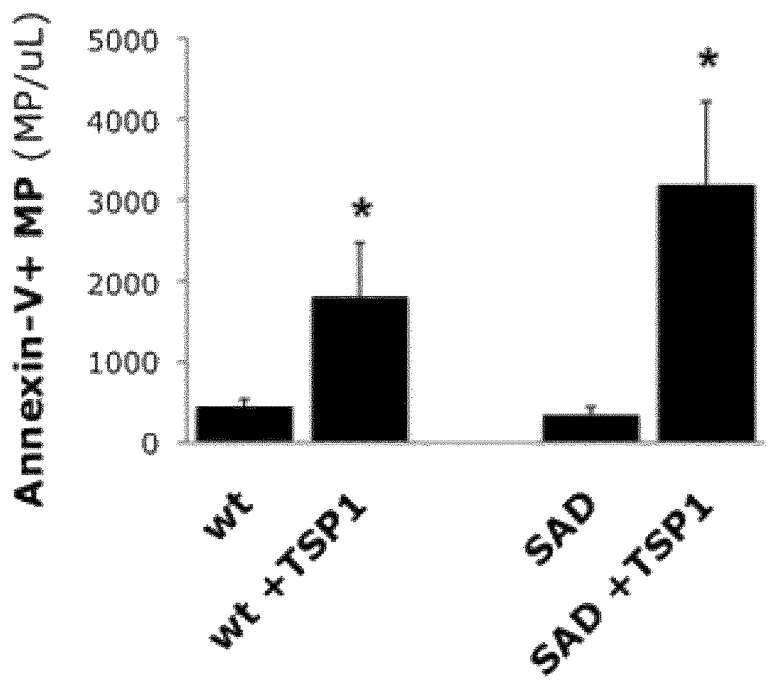

4 Claims, 12 Drawing Sheets
Specification includes a Sequence Listing.

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial
<220> FEATURE:
<223> OTHER INFORMATION: 4N1-1

<400> SEQUENCE: 1

Arg Phe Tyr Val Val Met Trp Lys
1               5

<210> SEQ ID NO 2
<211> LENGTH: 6
<212> TYPE: PRT
<213> ORGANISM: Artificial
<220> FEATURE:
<223> OTHER INFORMATION: 4N1-2

<400> SEQUENCE: 2

Arg Phe Tyr Val Val Met
1               5

<210> SEQ ID NO 3
<211> LENGTH: 8
<212> TYPE: PRT
<213> ORGANISM: Artificial
```

-continued

```
<220> FEATURE:
<223> OTHER INFORMATION: 4NGG

<400> SEQUENCE: 3

Arg Phe Tyr Gly Gly Met Trp Lys
1               5
```

METHODS FOR TREATING VASO-OCCLUSIVE CRISIS USING NON-MODIFIED ANNEXIN V

FIELD OF THE INVENTION

The present invention relates to methods for determining the risk of severe complications in hemolytic diseases. More particularly the present invention relates to a method for determining whether a patient suffering from sickle cell disease is at risk for a vaso-occlusive crisis.

BACKGROUND OF THE INVENTION

Sickle cell disease (SCD) is the first genetic disease and a public health challenge in France. SCD was designated public health priority by UNESCO in 2003, the French Ministry of Health in 2004 and WHO in 2006. Although a rare disease, the affliction is a worsening challenge for health and social services. A sharp increase in patient numbers put sickle cell disease at the top position of genetic diseases in French metropolitan areas, concerning 5,000 to 6,000 patients up to 18 yo, with an estimated 20,000 patients by 2020. Carrier frequency reaches 12% in French West Indies and rises in the USA and developed countries. Demographic trends and the systematic diagnosis at birth for ethnics at risk are partly responsible for this sharp increase in cases to treat. SCD, the most common genetic disease of our time, will soon become a public health challenge in western countries and France in particular.

SCD results from a point mutation (HbS) in the hemoglobin gene, causing hemoglobin to polymerize, mediating drastic and irreversible remodeling of red blood cells (RBC). Here, sickle cell disease refers to the homozygous HbSS phenotype. Remodeled RBC aggregate and become trapped in microvessels, favoring painful vaso-occlusive crises (VOC). Ensuing hemolysis liberates 'free' hemoglobin and heme into the bloodstream, and RBC membrane fragments called microparticles (MP), which carry adhesion receptors and bind avidly to vascular and circulating cells. The mechanisms that rule over the occurence of VOC and hemolysis are not known in SCD.

There are virtually no specific drugs to treat or prevent VOC. Primary care for VOC is hospitalization to manage pain with powerful analgesics, combined with rehydration and oxygenation. No specific drug exists to prevent the occurrence or treat VOC. Long term hydroxy-urea treatment (since 1995) is sometimes prescribed to force the re-expression of fetal hemoglobin, to reduce sickle cell formation and ultimately reduce hemolysis. However, hydroxy-urea is only effective in about 40% of SCD patients, with presumptions of carcinogenesis in the long term. The most severe cases of VOC are eligible for blood transfusion, with the associated exposure to viral infection and secondary hemochromatosis, and complications connected to transplantation. Hence, the burden of SCD on health institutions is bound to increase steeply worldwide. At this stage, gene medicine remains unable to correct the HbS mutations in adults, and advances in the prevention of RBC hemolysis have stagnated since the discovery of hydroxy-urea.

The physiopathology of SCD involves an intricate combination of circulating and cardiovascular factors that have only been envisaged recently. The primary focus has been the biology of the erythrocyte for the past decades, aimed at blocking RBC remodeling to prevent anemia.

There are virtually no tests or indices predictive of VOC, or of vascular injury, or of the development of severe complications of the disease, besides clinical indicators that are generally identified properly only when the VOC has begun or when complications are already advanced. Futhermore, there are very few tool to identify properly the pstable patients that may best benefit from the current treatments such as blood transfusion programmes or hydoxyurea. Managing the side effects associated to these treatments remains challenging.

Amazingly, very little research efforts have been made regarding the toxic byproducts of hemolysis and their contribution to the disease. Poor understanding of the disease limits the development of novel therapeutic strategies.

SUMMARY OF THE INVENTION

The present invention relates to methods for determining the risk of developing vaso-occlusives crises, vascular injury and severe degenerative complications in hemolytic diseases.

The present invention relates to a method for determining whether a patient suffering from sickle cell disease is at risk for a vaso-occlusive crisis comprising the steps consisting of i) determining the level of cell microparticles in a blood sample obtained from said patient, and ii) determining the level of heme and/or hemoglobin contained in said cell microparticles.

The present invention also relates to a method for determining whether a patient suffering from sickle cell disease is at risk for a vaso-occlusive crisis comprising the steps consisting of i) determining the level of cell microparticles in a blood sample obtained from said patient, and ii) determining the level of heme and/or hemoglobin contained in said cell microparticles and iii) determining the the level of heme and/or hemoglobin totally contained in the blood sample The present invention also relates to a method for determining whether a patient suffering from a hemolytic disease is at risk for vascular injury comprising the steps consisting of i) determining the level of circulating microparticles in a blood sample obtained from said patient, and ii) determining the level of heme and/or hemoglobin contained in said cell microparticles and iii) determining the level of heme and/or hemoglobin totally contained in said blood sample.

The present invention also relates to a method for determining whether a patient suffering from a hemolytic disease is at risk for generative complications comprising the steps consisting of i) determining the level of circulating microparticles in a blood sample obtained from said patient, and ii) determining the level of heme and/or hemoglobin contained in said cell microparticles and iii) determining the level of heme and/or hemoglobin totally contained in said blood sample.

The present invention also relates to a method for preventing a vaso-occlusive crisis in a patient suffering from sickle cell disease comprising depleting the blood-borne microparticles laden in heme and hemoglobin from the blood of said patient.

The present invention also relates to a method for limiting vascular injury in a patient suffering from hemolysis comprising depleting the blood-borne microparticles laden in heme and hemoglobin from the blood of said patient.

DETAILED DESCRIPTION OF THE INVENTION

In SCD, there is an admitted connection between hemolysis and the emergence of circulating microparticles. The molecular basis of this observation is entirely obscure. It is thought that trapped RBC rupture, presumably under the action of blood pressure, empty their contents into the bloodstream. On this basis, studies have shown that 'free' hemoglobin and 'free' heme in the plasma are scavenged after binding to specialized proteins, hemopexin for heme, and haptoglobin for hemoglobin. These molecular interactions mediate the recruitment of hemoglobin and heme into the liver and towards macrophages for the proper recycling of iron.

However, the inventors demonstrate that a significant part of 'free' heme and hemoglobin is not free in sickle cell disease plasma, but bound to microparticles (nearly all of plasma hemoglobin and heme), and particularly to microparticles carrying extra-cellular markers of erythrocytes. This is different from healthy patients without hemolysis who have low levels of circulating microparticles loaded with heme or hemoglobin. Furthermore, these heme- and hemoglobin-loaded microparticles are particularly deleterious to the vascular endothelium. The current concepts of heme and hemoglobin metabolism and their action on other cells in the vescular wall or in the circulation are thus drastically questioned by the findings. The data also opens new opportunities for the characterization and stratification of patients with sickle cell disease or other disease associated with hemolysis, including those associated with low-level or sub-clinical hemolysis.

The inventors have demonstrated a practical method to evaluate the relative charge of circulating or experimental microparticles in heme and hemoglobin.

The invention is a novel technique to characterize patients with sickle cell disease, other major hemolytic syndromes, or diseases otherwise associated with hemolysis. The technique aims at helping the diagnosis of the severity of vaso-occlusive crises, and the likeliness to develop complications associated with vascular dysfunction, vascular injury and vascular remodeling.

The invention may also be useful to help predict the occurrence of vaso-occlusive crises, and better characterize their severity. The invention may also be useful to provide patients at risk with better, more appropriate and more immediate care. The invention may also be useful to help therapeutic decision making and to better manage the side effects associated with current treatments for hemolytic disorders, including blood transfusion programs and hydroxyura.

The invention also describes a novel method to generate experimental microparticles from circulating cells, which can then be characterized to help diagnose the severity of vaso-occlusive crises, and the likeliness to develop complications associated with vascular dysfunction, vascular injury and vascular remodeling.

The inventors demonstrated that microparticles in the plasma from sickle cell disease can be separated by ultra-centrifugation. The inventors have shown that separating and discarding said microparticles by ultracentrifugation also removes a significant proportion of heme present in plasma. The inventors have shown that the level and the proportion of heme associated with microparticles is particularly elevated in sickle cell disease plasma. Hence patients that suffer from vaso-occlusive crises and vascular injury display high levels of microparticle-associated heme. The inventors confirmed these observations in plasma from transgenic SAD mice suffering from a murine form of sickle cell disease, compared to healthy mice. Futhermore, the inventors found that removing circulating microparticles by filtration (0.1 mm pore size) is also efficient to deplete a significant part of heme in sickle cell disease plasma.

The inventors demonstrated that specific peptides of a sequence derived from the carboxyterminus of thrombospondine-1 trigger the formation and shedding of MP by red blood cells. Circulating levels of TSP1 had previously been described as elevated in sickle cell disease patients at rest and elevated even further during VOC. Treating red blood cells with the TSP1 peptides also triggered the release of heme and hemoglobin out of the red blood cells, into the supernatant, in parallel to microparticle shedding. Ultracentrifugation experiments with treated red blood cell samples prepared as above demonstrated that virtually all released heme and hemoglobin is in fact depleted when MP are removed. Hence, the MP shed by red blood cells with the technique appear very similar to circulating MP in sickle cell disease in terms of heme and hemoglobin contents, they are representative of circulating microparticles in steady state patients and microparticles that could be shed during VOC.

The inventors demonstrated that microparticle preparations generated from diseased red blood cells do not always bear the same characteristics (size, granulosity, cell surface determinants, toxicity for the endothelium), nor carry the same loads of heme and hemoglobin. They also showed that microparticles shed by red blood cells purified from a selected individual using said technique have specific characteristics that other MP generated by different means do not always share.

Hence, microparticles generated by said technique or purified from body fluids could be used for the diagnosis of the severity of sickle cell disease, for the diagnosis of vascular injury, and for the prognostic of further VOC as well as degenerative complications.

Furthermore, the inventors demonstrated that heme- and hemoglobin-laden MP are toxic for cultured endothelium, inducing more radical oxygen species production and more apoptosis. Moreover, microparticles released by sickle cell disease red blood cells were more toxic for cultured endothelium, inducing more radical oxygen species production and more apoptosis. The inventors also demonstrated that synthetic microparticles made with phosphatidylcholine and phosphatidylserine, artificially loaded with heme, are particularly toxic for cultured endothelium, inducing more radical oxygen species production and more apoptosis than synthetic microparticles devoid of heme or hemoglobin.

The inventors also showed that mesenteric micro-arteries perfused with heme-loaded microparticles loose their ability to vasodilate in response to acethycholine, consistent with vascular injury and endothelial dysfunction.

The inventors also demonstrated that heme- and hemoglobin-laden MP are toxic for red blood cells, favor their aggregation and enhance the bonds linking them to each other.

Heme- and hemoglobin-laden MP function as information vectors from a parent cell to a target cell, carrying toxic moieties and potentiating their effects on target cells.

Heme- and hemoglobin-laden MP may thus participate in the induction of VOC by promoting small vessel obstruction by red blood cell and red blood cell fragment aggregates. Indeed, the inventors have found that the intravascular injection of purified heme-loaded microparticles to transgenic SAD mice suffering from a murine form of sickle cell disease is sufficient to trigger immediate VOC, characterized by a drastic drop in the perfusion of sensitive organs such as kidneys.

Furthermore, the inventors went on to demonstrate that heme- and hemoglobin-laden MP are toxic for the endothelium and promote the adhesion of red blood cells to vascular endothelial cells. Hence heme- and hemoglobin-laden MP may promote the anchorage of red blood cell aggregates to the vascular wall and further enhance the plugging of small vessels. Moreover, heme- and hemoglobin-laden MP my favor deposits of red blood cells, red blood cell membranes or red blood cell fragments against the wall of blood vessels.

Thus, the inventors demonstrated for the first time that heme- and hemoglobin-laden MP have several of the specific characteristics necessary to enhance or even trigger VOC in sickle cell disease.

Finally, the intravenous injection of red blood cell MP to SAD transgenic mice with sickle cell disease provided the in vivo demonstration that heme- and hemoglobin-laden MP triggered immediate VOC, as revealed by a local increase in vascular resistance in specific territories such as the kidney.

The inventors have also demonstrated that the 'free' heme and 'free' hemoglobin present in plasma can be virtually entirely depleted from plasma by ultracentrifugation. This finding suggests that therapeutic benefits may be obtained by the specific depletion of patient plasma from heme- and hemoglobin-laden MP.

The quantification of MP levels coupled to the evaluation of their relative contents in heme and hemoglobin can thus be used as a novel clinical index of disease severity, predictive of vascular damage, remodeling and dysfunction. This index may help better diagnose and stratify patients according to the predicted severity of their disease and the likeliness to develop severe complications associated with sickle cell disease.

In a context particularly poor in diagnosis methods, therapeutic tools and therapeutic innovations, the characterization of the levels of heme- and hemoglobin-carrying microparticles, as well as their relative contents in heme and hemoglobin may constitute a major improvement for the care of patients with sickle cell disease, major hemolytic disorders and other diseases associated with hemolysis.

Diagnostic and Prognostic Methods of the Invention

The present invention relates to a method for determining whether a patient suffering from sickle cell disease is at risk for a vaso-occlusive crisis comprising the steps consisting of i) determining the level of cell microparticles in a blood sample obtained from said patient and ii) determining the level of heme and/or hemoglobin contained in said cell microparticles.

The present invention relates to a method for determining whether a patient suffering from sickle cell disease is at risk for a vaso-occlusive crisis comprising the steps consisting of i) isolating the cell microparticles in a blood sample obtained from said patient and ii) determining the level of heme and/or hemoglobin contained in said cell microparticles.

In one embodiment, the methods as above described comprise the step consisting of ii) determining the level of heme and/or hemoglobin totally contained in the blood sample obtained from the patient. The expression "level of heme and/or hemoglobin totally contained in the blood sample" refers to the level of heme and/or hemoglobin that is free and associated with micropaticles in the blood sample.

The term "blood sample" means a whole blood, serum, or plasma sample obtained from the patient. Preferably the blood sample according to the invention is a plasma sample. A plasma sample may be obtained using methods well known in the art. For example, blood may be drawn from the patient following standard venipuncture procedure on trisodium citrate buffer. Plasma may then be obtained from the blood sample following standard procedures including but not limited to, centrifuging the blood sample at about 1,500*g for about 15-20 minutes (room temperature), followed by pipeting of the plasma layer. Platelet-free plasma (PFP) will be obtained following centrifugation at about 13,000*g for 5 min. In order to collect or discard the microparticles, the plasma sample may be centrifuged in a range of from about 15,000 to about 20,000*g. Preferably, the plasma sample is ultra-centrifuged at around 17,570*g at a temperature of about 4° C. Different buffers may be considered appropriate for resuspending the pelleted cellular debris, which contains the microparticles. Such buffers include reagent grade (distilled or deionized) water and phosphate buffered saline (PBS) pH 7.4. Preferably, PBS buffer (Sheath fluid) is used. More preferably, the blood sample obtained from the patient is a platelet free platelet sample (PFP) sample. PFP may be separated from 10 ml citrated whole blood drawn from the fistula-free arm, 72 hours after the last dialysis. PFP may be obtained after citrate blood centrifugation at 1500*g (15 min), followed by 13000*g centrifugation (5 min, room temperature).

As used herein, the term "cell microparticle" denotes a plasma membrane vesicle shed from an apoptotic, senescent or activated cell (Boulanger and Dignat-George, 2011, Arterioscler Thromb Vasc Biol. 2011;31:2-3). The size of cell microparticle ranges from 0.05 μm to 1 μm in diameter. Typically, said cell microparticle expresses different cell surface markers that are the same as the parent cells. According to the invention, microparticles are phosphatidylserine-positive microparticles.

Standard methods for isolating microparticles are well known in the art. For example the methods may consist in collecting the population of microparticles present in the blood sample as above prepared and using differential binding partners directed against the specific surface markers of the microparticles of interest, wherein microparticles are bound by said binding partners to said surface markers.

In a general manner, Annexin V binds to externalized phosphatidylserine in a clacium dependent manner and thus labels microparticles expressing phosphatidylserine irrespective of the cellular origin.

In a particular embodiment, the methods of the invention comprise contacting the blood sample with a set of binding partners capable of selectively interacting with microparticles present in said blood sample. The binding partner may be an antibody that may be polyclonal or monoclonal, preferably monoclonal, directed against the specific surface marker of the microparticles. In another embodiment, the binding partners may be a set of aptamers.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S.D., 1999. Peptide aptamers consist of conformationally constrained antibody variable regions displayed by a platform protein, such as *E. coli* Thioredoxin A, that are selected from combinatorial libraries by two hybrid methods.

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

Preferably, the antibodies against the surface markers are already conjugated to a fluorophore (e.g. FITC-conjugated and/or PE-conjugated). Examples include monoclonal anti-human CD62E-FITC, CDC105-FITC, CD51-FITC, CD106-PE, CD31-PE, and CD54-PE, available through Ancell Co. (Bayport, Minn.).

The aforementioned assays may involve the binding of the binding partners (ie. Antibodies or aptamers) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. The solid surfaces are preferably beads. Since microparticles have a diameter of roughly 0.05-1 µm, the beads for use in the present invention should have a diameter larger than Beads may be made of different materials, including but not limited to glass, plastic, polystyrene, and acrylic. In addition, the beads are preferably fluorescently labelled. In a preferred embodiment, fluorescent beads are those contained in TruCount™ tubes, available from Becton Dickinson Biosciences, (San Jose, Calif.).

According to the invention, methods of flow cytometry are preferred methods for determining the level of microparticles in the blood sample obtained from the patient. For example, fluorescence activated cell sorting (FACS) may be therefore used to separate in the blood sample as above described the desired microparticles. In another embodiment, magnetic beads may be used to isolate microparticles (MACS).

For instance, beads labelled with monoclonal specific antibodies may be used for the positive selection of microparticles. Other methods can include the isolation of microparticles by depletion the microparticles that are not of interest (negative selection).

Alternatively cell microparticle isolation methods may also consist in collecting the population of microparticles present in the blood sample of the cells and using size exclusion columns or filters to purify microparticles of specific sizes out of the blood sample as above prepared (filtration). Ultracentrifugation may also be performed, for example before filtration. For example, microparticles can be isolated from plasma by filtration, using 0.1 µm pore filters for instance.

Standard methods for the level of heme and hemoglobin are well known. Typically said levels may be determined by spectrophotometry. The classical method for determining the level of hemoglobin in a sample utilizes the method of Drabkin. (D. L. Drabkin and J. H. Austin, Spectre/photometric Studies, J. BIOL. CHEM., 112:51, 1935). Briefly, potassium ferricyanide is then added to the sample, which results in oxidation of the heme iron to, produce cyanomethemoglobin. Cyanide ions then convert the methemoglobin to cyanomethemoglobin, a more stable chromagen. The hemoglobin concentration of the sample is then determined by measuring the absorbance of the cyanomethemoglobin at 540 nm. An other method is also described in Kahn S E, Watkins B F, Bermes E W Jr (1981). Ann Clin Lab Sci 11:126-31; Fairbanks V F, Wiesmer S C, O'Brien P C (1992). Cli Chem 38:132-140. The EXAMPLE provides an illustration of the methods that may be used for determining the level of heme and hemoglobin contained in the microparticles isolated as above described. Another method consists at measuring absorbance at 575 nm, the wavelength of an absorption peak specific to heme and hemoglobin. Spectrophotometric methods preferably include an approach to correct for the enhanced turbidity of the plasmas in sickle cell disease and other hemolytic diseases. Such methods include substracting absorbance values measured at 600 nm or 650 nm.

In a particular embodiment, the levels determined by the present method are then compared to reference levels for determining whether the patient is a risk for a vaso-occlusive crises.

In one embodiment, the reference level refers to the levels of microparticles in blood sample obtained from a selected population of patient who underwent or not a vaso-occlusive crisis. For example, the reference level may be of the level of microparticles in blood sample obtained from patients who underwent a vaso-occlusive crisis. For example, the reference level may be of the level of microparticles in blood sample obtained from patients who did not undergo a vaso-occlusive crisis. The reference level can be a threshold value, or a range. The reference level can be established based upon comparative measurements between patients who underwent a vaso-occlusive crisis and patients who did not undergo a vaso-occlusive crisis.

In one embodiment, the reference level refers to the levels of heme and hemoglobin in the cell microparticle sample obtained from a selected population of patient who underwent or not a vaso-occlusive crisis. For example, the reference level may be of the level of heme and/or hemoglobin obtained from patients who underwent a vaso-occlusive crisis. For example, the reference level may be of the level of heme and/or hemoglobin obtained from patients who did not undergo a vaso-occlusive crisis. The reference level can be a threshold value, or a range. The reference level can be established based upon comparative measurements between patients who underwent a vaso-occlusive crisis and patients who did not undergo a vaso-occlusive crisis.

In one embodiment, the level of heme and/or hemoglobin contained in said microparticles is compared to the level of heme and/or hemoglobin totally contained in the blood sample, and the ratio accordingly determined indicates whether the patient is at risk for a vaso-occlusive crisis The combined measurement of the level of microparticles and the level of heme and/or hemoglobin contained in said microparticles and the level of heme and/or hemoglobin totally contained in the blood sample indicate whether the patient is at risk for a vaso-occlusive crisis.

In a further embodiment, the method of the present invention may further comprise a step consisting of determining whether said microparticles are toxic for the endothelium. Typically said step may be performed as described in the EXAMPLE. Briefly, endothelial cells may be incubated with said microparticles and toxicity toward said endothelial cells is then determined.

The method of the invention is thus suitable for the stratification of patients with the severity of vaso-occlusive crises and the extent of vascular injury. However the method of the invention may also particularly useful for determining whether a patient is at risk for a vasculopathy. Typically, said method may be useful to better diagnose patients afflicted with major hemolytic disorders, or other diseases associated with hemolysis. More particularly, the method of the invention may allow the stratification of patients with respect to their likeliness to develop complications associated with vascular damage, remodeling or dysfunction. These complications include:

- severe complications of sickle cell disease include severe chest syndrome in particular, as well as ischemic brain injury, retinopathy (retinal artery thrombosis), priapism.
- degenerative complications include aseptic osteonecrosis, retinopathy, nephropathy (including renal insufficiency), pulmonary hypertension, cardiac insufficiency, skin ulcerations.
- other complications include spells of septicemia, sudden deafness, severe anemia (blood hemoglobin <6 g/dl)
- Vascular injury includes endothelial dysfunction, impaired vasodilation and capillary rarefaction, hypertension, vascular parietal thickening and atherosclerosis.

Accordingly the present invention relates to a method for determining whether a patient is at risk for severe complication in hemolytic diseases comprising the steps consisting of i) determining the level of cell microparticles in a blood sample obtained from said patient and ii) determining the level of heme and/or hemoglobin contained in said cell microparticles.

The present invention also relates to a kit or an apparatus for performing the methods of the present invention comprising means for isolating microparticles from a blood sample, means for quantifying said microparticles and means for determining the the level of heme and/or hemoglobin contained in said cell microparticles Therapeutic Methods of the Invention The present invention also relates to a method for preventing a vaso-occlusive crisis in a patient afflicted with by sickle cell disease comprising depleting the blood-borne microparticles laden in heme and hemoglobin from the blood of said patient.

Typically, the patient has been determined at risk for a vaso-occlusive crisis by the diagnostic method of the invention as above described.

Depletion of the blood-borne microparticles laden in heme or hemoglobin may be performed by any well-known method in the art. Typically, plasmapheresis coupled to ultracentrifugation may be used.

The therapeutic method of the invention may also be applied to patient who has been determined at risk for a vasculopathy as above described.

The present invention also relates to a method for preventing or treating a vaso-occlusive crisis in a patient suffering from sickle cell disease comprising the step of administering said patient with an agent selected from the group consisting of a phosphatidylserine receptor antagonist (such as recombinant annaxin a5 or anti-Del-1 neutralizing antibodies) or an inhibitor of phosphatidylserine receptor expression.

The present invention also relates to a method for preventing or treating vascular complications in patients afflicted with major hemolytic disorders comprising the step of administering said patient with an agent selected from the group consisting of a phosphatidylserine receptor antagonist or an inhibitor of phosphatidylserine receptor expression.

The term "phophatidylserine" has its general meaning in the art and refers to the most abundant negatively charged phospholipid in eukaryotic membranes. Phophatidylserine refers to the anionic phospholipid present exclusively in the inner leaflet of the plasma membrane of a normal cell, phophatidylserine is externalized following cell activation with both physiological and pathologic stimuli such apoptosis.

As used herein the term "phosphatidylserine receptor antagonist" refers to any agent that inhibits the binding of phosphatidylserine to phosphatidylserine receptor. Said antagonist may be selected form the group consisting of small molecule, antibodies, aptamers, and polypeptides.

The phosphatidylserine receptor antagonist may consist in an antibody or antibody fragment directed against phosphatidylserine or phosphatidylserine receptor. As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies may be prepared according to conventional methodology. Monoclonal antibodies may be generated using the method of Kohler and Milstein (1975). To prepare monoclonal antibodies useful in the invention, a mouse or other appropriate host animal is immunized at suitable intervals (e.g., twice-weekly, weekly, twice-monthly or monthly) with antigenic forms of phosphatidylserine receptor. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in phosphatidylserine receptor. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., (1999), the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab')2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "nanobody®". According to the invention, sdAb can particularly be llama sdAb.

Then after raising antibodies directed against phosphatidylserine or phosphatidylserine receptors as above described, the skilled man in the art can easily select those inhibiting binding of phosphatidylserine to phosphatidylserine receptor.

In another embodiment the phosphatidylserine receptor antagonist is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods. Then after raising aptamers directed against phosphatidylserine receptors as above described, the skilled man in the art can easily select those inhibiting phosphatidylserine receptor.

In another embodiment, the phosphatidylserine receptor antagonist is a polypeptide, especially a polypeptide having the ability to bind posphatidylserine.

In one embodiment of the invention, the polypeptide derives from a polypeptide selected from the group consisting of annexin V, annexin peptides, synaptotagmin I, lactadherin, T cell immunoglobulin mucin 1 and 4 (TIM-1, TIM-4), c-carboxyglutamic acid (Gla) containing proteins such as vitamin K-dependent blood coagulation factors.

In another embodiment, of the invention, the phosphatidylserine receptor antagonist is a modified annexin V polypeptide.

In another embodiment of the invention, the modified annexin V polypeptide is a polymer of annexin V that has an increased effective size. It is believed that the increase in effective size results in prolonged half-life in the vascular compartment. One such modified annexin V is a dimer of annexin V. In one embodiment, the dimer of annexin V is a homodimer of annexin V. Said homodimer of human annexin V may prepared in using well-established methods of recombinant DNA technology. The annexin V molecules of the homodimer are joined through peptide bonds to a flexible linker. In some embodiments, the flexible linker contains a sequence of amino acids flanked by a glycine and a serine residue at either end to serve as swivels. The linker preferably comprises one or more such "swivels." Preferably, the linker comprises 2 swivels which may be separated by at least 2 amino acids, more particularly by at least 4 amino acids, more particularly by at least 6 amino acids, more particularly by at least 8 amino acids, more particularly by at least 10 amino acids. Preferably, the overall length of the linker is 5-30 amino acids, 5-20 amino acids, 5-10 amino acids, 10-15 amino acids, or 10-20 amino acids. The dimer can fold in such a way that the convex surfaces of the monomer which bind phosphatidylserine, can both gain access to externalized phosphatidylserine. Flexible linkers are well known in the art. Typically a homodimer of annexin V is diannexin as described in Kuypers F A, Larkin S K, Emeis J J, Allison A C. Interaction of an annexin V homodimer (Diannexin) with phosphatidylserine on cell surfaces and consequent antithrombotic activity. Thromb Haemost. 2007 March;97(3):478-86.

In another embodiment of the invention, modified annexin V polypeptide may consist on a recombinant annexin V expressed with, or chemically coupled to, another protein such as the Fc portion of immunoglobulin. Such expression or coupling increases the effective size of the molecule, preventing the loss of annexin V from the vascular compartment and prolonging the half life of said modified annexin V polypetide.

In a particular embodiment the polypeptide is a functional equivalent of phosphatidylserine receptor. As used herein, a "functional equivalent of phosphatidylserine receptor" is a compound which is capable of binding to phosphatidylserine, thereby preventing its interaction with phosphatidylserine receptor. The term "functional equivalent" includes fragments, mutants, and muteins of phosphatidylserine receptor. The term "functionally equivalent" thus includes any equivalent of phosphatidylserine receptor obtained by altering the amino acid sequence, for example by one or more amino acid deletions, substitutions or additions such that the protein analogue retains the ability to bind to phosphatidylserine. Amino acid substitutions may be made, for example, by point mutation of the DNA encoding the amino acid sequence.

Functional equivalents include molecules that bind phosphatidylserine and comprise all or a portion of the extracellular domains of phosphatidylserine receptor. Typically, said functional equivalents may comprise binding domain of phosphatidylserine receptor or a portion thereof.

The functional equivalents include soluble forms of the phosphatidylserine receptor. A suitable soluble form of these proteins, or functional equivalents thereof, might comprise, for example, a truncated form of the protein from which the transmembrane domain has been removed by chemical, proteolytic or recombinant methods.

Preferably, the functional equivalent is at least 80% homologous to the corresponding protein. In a preferred embodiment, the functional equivalent is at least 90% homologous as assessed by any conventional analysis algorithm such as for example, the Pileup sequence analysis software (Program Manual for the Wisconsin Package, 1996).

The term "a functionally equivalent fragment" as used herein also may mean any fragment or assembly of fragments of phosphatidylserine receptor that binds to phosphatidylserine. Accordingly the present invention provides a polypeptide capable of inhibiting binding of phosphatidylserine receptor to phosphatidylserine, which polypeptide comprises consecutive amino acids having a sequence which corresponds to the sequence of at least a portion of an extracellular domain of phosphatidylserine receptor, which portion binds to phosphatidylserine.

Functionally equivalent fragments may belong to the same protein family as the human phosphatidylserine receptor identified herein. By "protein family" is meant a group of proteins that share a common function and exhibit common sequence homology. Homologous proteins may be derived from non-human species. Preferably, the homology between functionally equivalent protein sequences is at least 25% across the whole of amino acid sequence of the complete protein. More preferably, the homology is at least 50%, even more preferably 75% across the whole of amino acid sequence of the protein or protein fragment. More preferably, homology is greater than 80% across the whole of the sequence. More preferably, homology is greater than 90% across the whole of the sequence. More preferably, homology is greater than 95% across the whole of the sequence.

The polypeptides of the invention may be produced by any suitable means, as will be apparent to those of skill in the art. In order to produce sufficient amounts of polypeptides of the invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known.

When expressed in recombinant form, the polypeptide is preferably generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may b e manipulated and grown. A common, preferred bacterial host is E coli.

In specific embodiments, it is contemplated that polypeptides used in the therapeutic methods of the present invention may be modified in order to improve their therapeutic efficacy. Such modification may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., phosphatidylserine receptor) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit the expression of a gene.

Inhibitors of phosphatidylserine receptor expression for use in the present invention may be based on antisense oligonucleotide constructs. Anti-sense oligonucleotides, including anti-sense RNA molecules and anti-sense DNA molecules, would act to directly block the translation of phosphatidylserine receptor mRNA by binding thereto and thus preventing protein translation or increasing mRNA degradation, thus decreasing the level of phosphatidylserine receptor proteins, and thus activity, in a cell. For example, antisense oligonucleotides of at least about 15 bases and complementary to unique regions of the mRNA transcript sequence encoding phosphatidylserine receptor can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of phosphatidylserine receptor expression for use in the present invention. phosphatidylserine receptor gene expression can be reduced by contacting the patient or cell with a small double stranded RNA (dsRNA), or a vector or construct causing the production of a small double stranded RNA, such that phosphatidylserine receptor expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of phosphatidylserine receptor expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of phosphatidylserine receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of phosphatidylserine receptor expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing phosphatidylserine receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER ("A Laboratory Manual," W. H. Freeman C. O., New York, 1990) and in MURRY ("Methods in Molecular Biology," vol.7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

The invention will be further illustrated by the following figures and examples. However, these examples and figures should not be interpreted in any way as limiting the scope of the present invention.

Figures:

FIG. 1: Shedding of MP in the blood of SAD transgenic mice, in vivo. We injected recombinant TSP1 (1.3 mg/kg) intravenously (retro-orbital) to wild type or SAD transgenic mice with sickle cell disease. After 5 to 10 minutes, we collected heparinized mouse blood, and prepared platelet-free plasma (PFP). We quantified circulating MP by FACS after labeling with fluorescent annexin-V, a phoshatidylserine ligand, compared with calibrated fluorescent microbeads. (*) $p<0.05$ versus 'wt'.

Figure 2A:
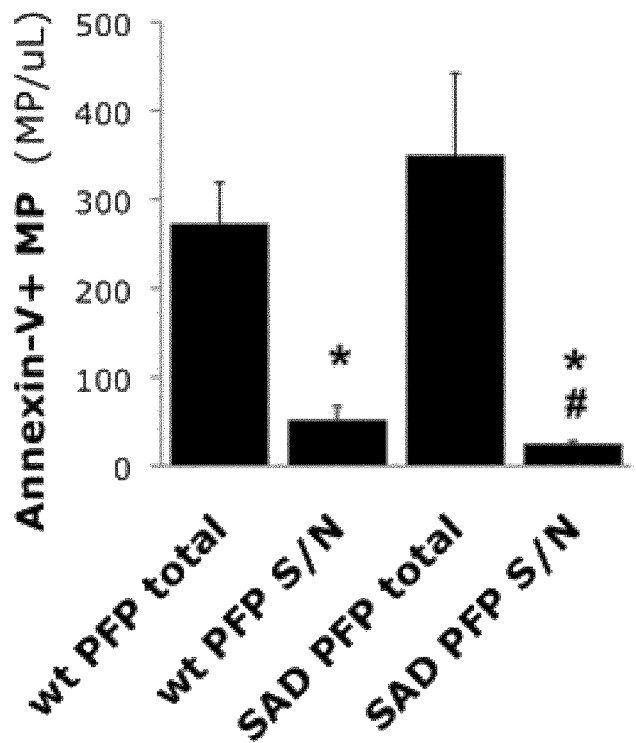
Figure 2B:
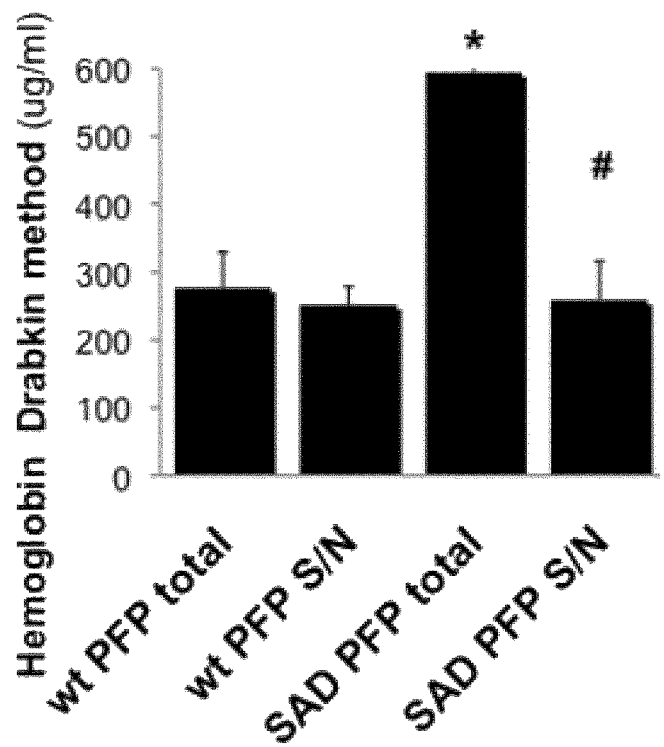

FIG. 2: Circulating MP in WT and SAD mice: Heme contents: Plasma MP and 'free' heme. We prepared platelet-free plasma (PFP) from fresh heparinized wt or SAD mouse blood. We treated half the samples by ultracentrifugation (20800 g for 4 hours at 4° C.) to pellet circulating MP, which we discarded. We measured 'free' heme in plasma before and after depletion of MP by ultracentrifugation. (A) Quantification of MP by FACS after labeling with fluorescent annexin-V, a cell surface phosphatidylserine ligand, in comparaison with calibrated fluorescent microbeads, (B) quantification of 'free' heme by the drabkin method. (*) $p<0.05$ versus 'total', (#) $p<0.05$ versus 'wt'.

Figure 3A:
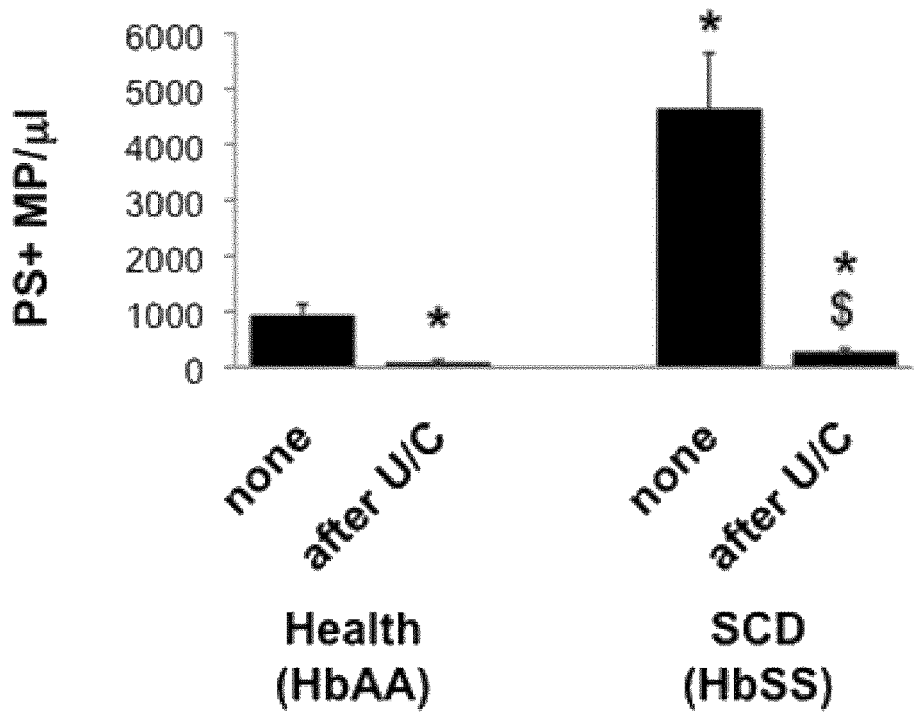
Figure 3B:
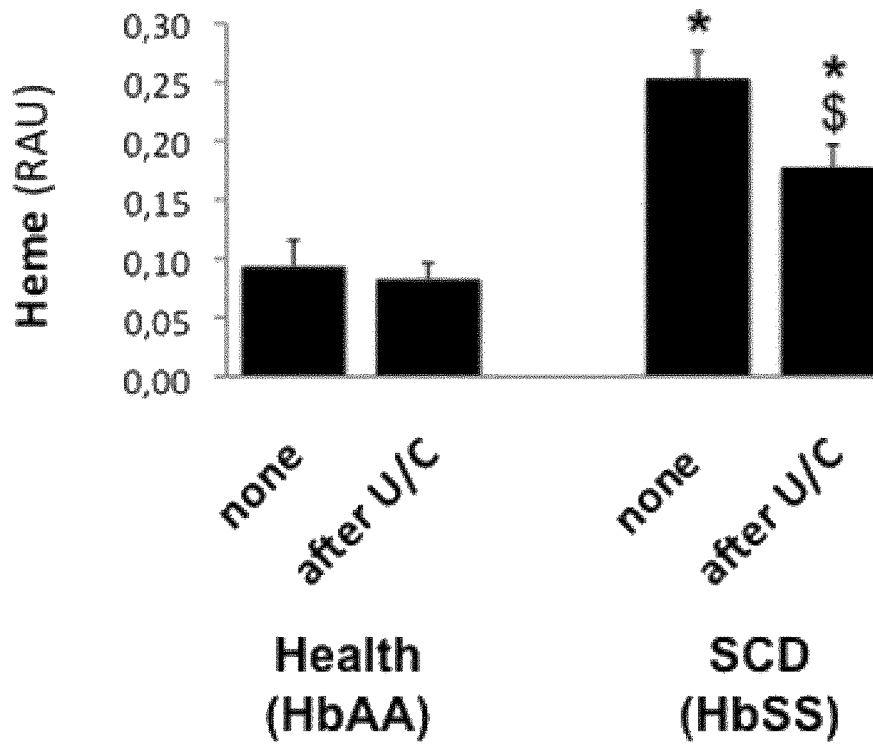

FIG. 3: Circulating MP in healthy Human and SCD plasma : Heme contents. We prepared platelet-free plasma (PFP) from fresh heparinized healthy Human or SCD blood. In some cases, we treated the samples by ultracentrifugation (20800 g for 4 hours at 4° C.) to pellet circulating MP, which we discarded, keeping the supernatant. We performed several measures of heme by spectrophotometry before and after depletion of MP by this ultracentrifugation method: Quantification of MP by FACS after labeling with fluorescent annexin-V, a cell surface phosphatidylserine ligand was compared to calibrated fluorescent microbeads. (B) 'Free' heme was quantified by spectrophotometry was performed at 575 nm. Turbidity was compensated for by substraction of the absorbance at 650 nm. Data expressed in relative absorbance units (RAU). (*) $p<0.05$ versus 'none' in healthy plasmas; ($) $p<0.05$ versus 'none' in SCD plasmas (before ultra-centrifugation (U/C).

FIG. 4: Shedding of MP by RBC in vitro: Validation of heme quantification methods. Heme measurements in vitro. We prepared suspensions of red blood cells from fresh heparinized WT and SAD mouse blood. Red blood cells were then incubated with peptide 4N1-1 at 25 mM for 30 minutes. We collected the supernatants (S/N) and ultracentrifuged them at 20800 g for 4 hours at 4° C. to pellet MP which were discarded. We performed several measures before and after depletion of MP: Quantification of 'free' heme by spectrophotometry at 540 nm or 575 nm, by the Drabkin method, by the Kahn method, by the AI method, by the AI II method. (*) $p<0.05$ versus 'total' (before depletion of MP); (#) $p<0.05$ versus '4N1-1 total' (after 4N1-1, and before depletion of MP). A) Absorbance at 540 nm, B) Absorbance at 575 nm, C) Drabkin method, D) Kahn method, E) AI method, F) AI II method.

Figure 5A:
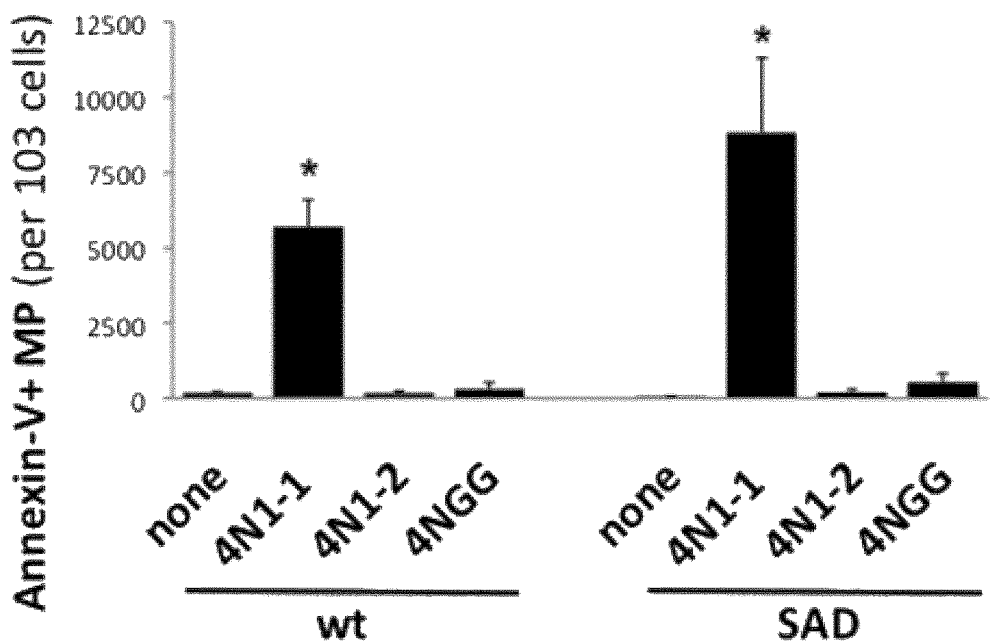
Figure 5B:
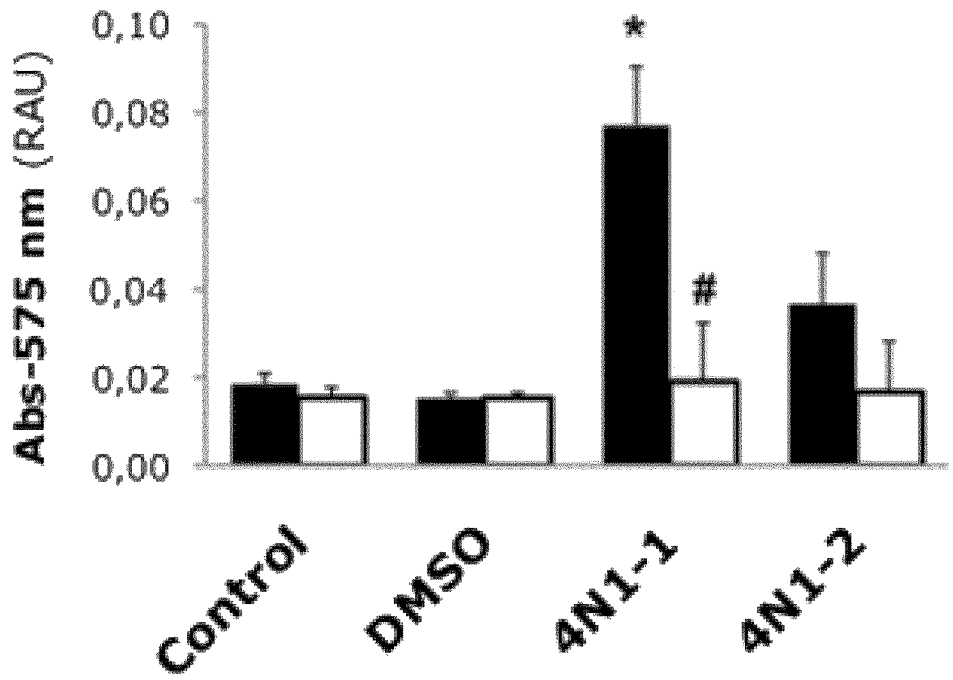

FIG. 5: MP shedding by mouse red blood cells, in vitro. Red blood cells freshly harvested from wild type and SAD mice were washed and resuspended in RPMI-1640 medium at $2\times10^6$ cells/ml. Red blood cells were then incubated for 30 minutes with peptides derived from the thrombospondine-1 carboxyterminus, including the CD47 receptor agonist 4N1-1, or the truncated peptide 4N1-2, or the mutated peptide 4 NGG, all at 25 mM. We collected the supernatants (S/N) and (A) quantified MP after labeling with fluorescent annexin-V, compared with calibrated fluorescent microbeads. Alternatively (B), we quantified heme (Absorbance at 575 nm) released by wild type red blood cells in the supernatant, before (black bars) and after (white bars)depletion of the microparticles by ultracentrifugation (20500 g for 4 hours). (*) $p<0.05$ versus 'none' (control). (#) $p<0.05$ versus '4N1-1' before depletion of the microparticles.

Figure 6:
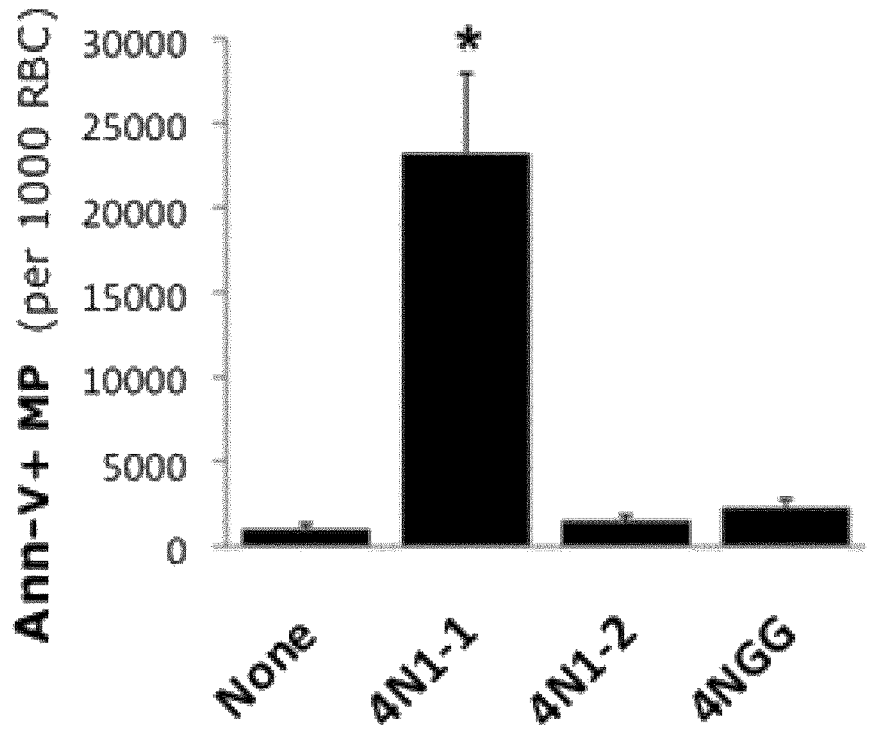

FIG. 6: MP shedding by Human red blood cells, in vitro. Red blood cells freshly harvested from healthy human blood were washed and resuspended in RPMI-1640 medium at $2\times10^6$ cells/ml. Red blood cells were then incubated for 30 minutes with peptides derived from the thrombospondine-1 carboxyterminus, including the CD47 receptor agonist 4N1-

1, or the truncated peptide 4N1-2, or the mutated peptide 4 NGG, all at 25 mM. We collected the supernatants (S/N) and quantified MP after labeling with fluorescent annexin-V, compared with calibrated fluorescent microbeads. (*) p<0.05 versus 'none'.

Figure 7:
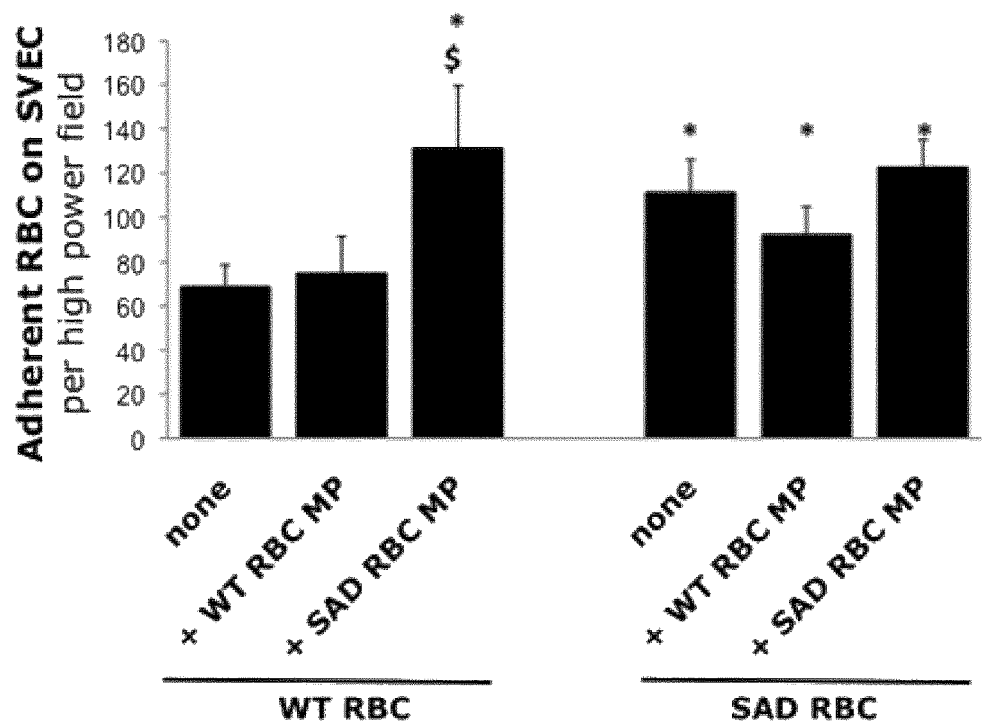

FIG. 7: Endothelium: Red blood cell adhesion in response to WT and SAD mouse red blood cell MP. Confluent SVEC4-10 endothelial cells were incubated for 2 hours with MP (25 MP/ml) shed by WT or SAD mouse red blood cells. After removing the unbound MP and washing the endothelial monolayer, fresh mouse red blood cells from WT or SAD (106/ml) were left to adhere for 30 minutes. Unbound cells were then removed, and adherent red blood cells were counted. (*) p<0.05 versus 'none', ($) p<0.05 versus 'wt RBC MP'.

Figure 8:
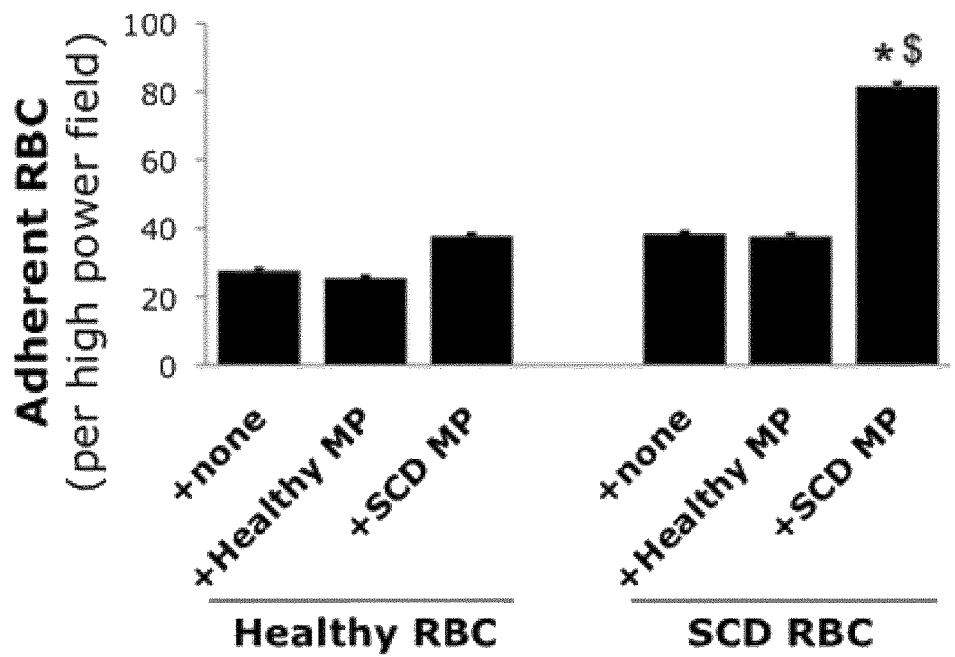

FIG. 8: Endothelium : Red blood cell adhesion in response to Human healthy or SCD red blood cell MP. Confluent HUVEC endothelial cells were incubated for 2 hours with MP (25 MP/ml) shed by healthy Human or SCD red blood cells. After removing the MP and washing the endothelial monolayer, fresh Human red blood cells from healthy Human or SCD patients(106/ml) were left to adhere for 30 minutes. Non adherent cells were then removed, and adherent cells were counted. (*) p<0.05 versus 'none'; ($) p<0.05 versus healthy RBC ahderent to endothelium pre-treated with SCD RBC MP.

Figure 9:
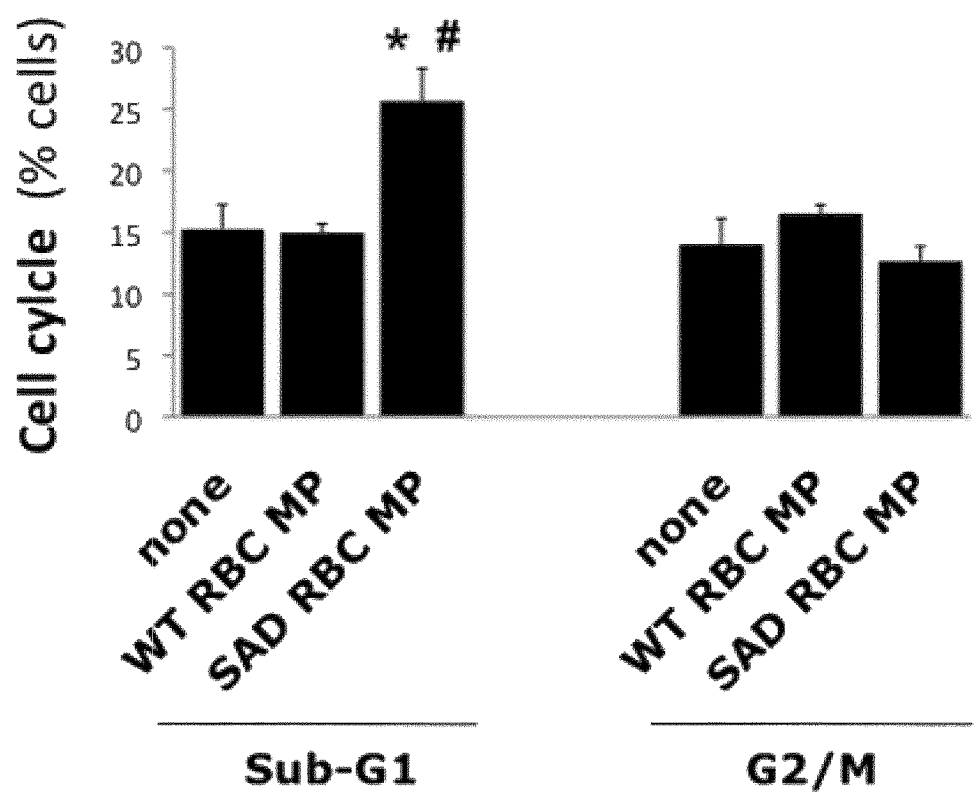

FIG. 9: Endothelium: Apoptosis in the presence of WT and SAD mouse red blood cell MP. Confluent SVEC4-10 endothelial cells were incubated for 24 hours in presence of 0.5% serum and MP shed by WT or SAD red blood cells (25 MP/ml). After removing the MP and washing the endothelial monolayer, endothelial cells were then collected by short trypsinization and fixed with paraformaldhehyde and labeled with propidium iodide to quantify their total contents in DNA by FACS. (*) p<0.05 versus 'none'; (#) p<0.05 versus 'wt RBC MP'.

Figure 10:
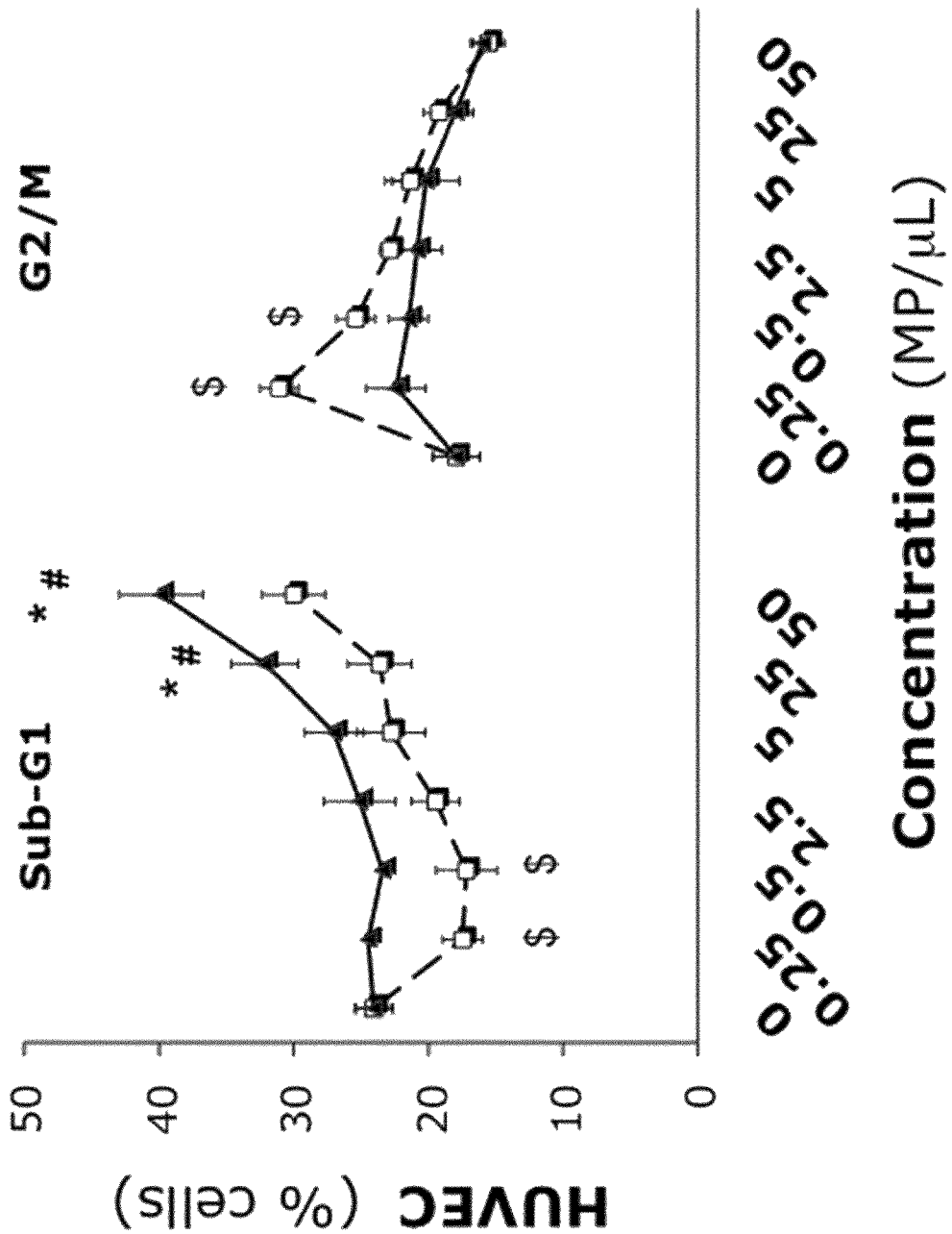

FIG. 10: Endothelium : Apoptosis in the presence of healthy Human or SCD red blood cell MP. Confluent HUVEC endothelial cells were incubated for 24 hours in presence of 0.5% serum and MP shed by healthy Human red blood cell MP (hashed line) or SCD red blood cell MP (solid line) from 0 to 50 MP/ml. After removing unbound MP and washing the endothelial monolayer, endothelial cells were then collected by short trypsinization, fixed with para-formaldehyde and labeled with propidium iodide to quantify total DNA contents by FACS. Sub-G1 phase designated apoptosis, G2/M designated proliferative cells. (*) p<0.05 versus 'none' (0) ; (#) p<0.05 versus 'healthry RBC MP'; ($) p<0.05 versus 'SCD RBC MP'.

Figure 11:
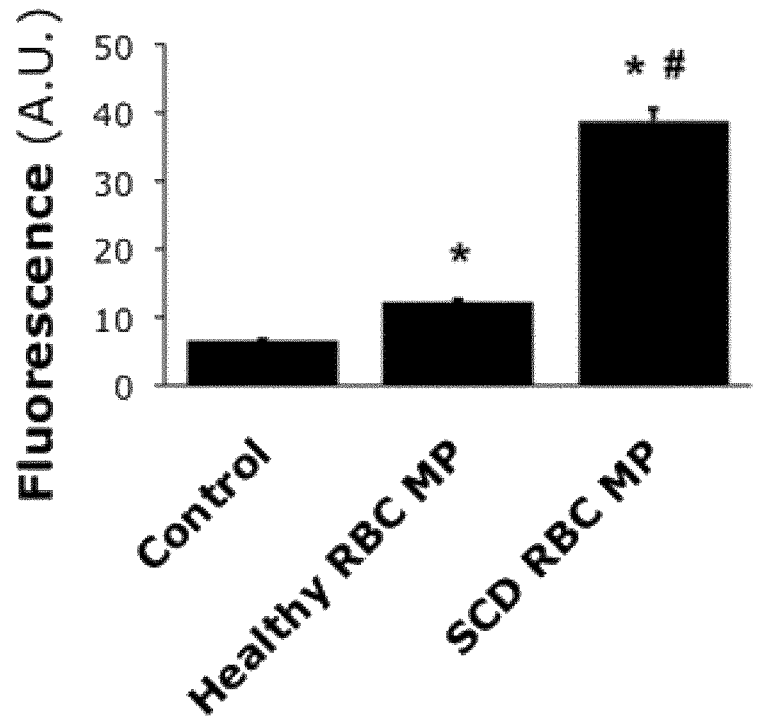

FIG. 11: Endothelium: Radical oxygen species generation in response to Human healthy or SCD red blood cell MP. Confluent HUVEC endothelial cells were incubated for 2 hours in the absence (none) or presence of MP shed by healthy Human red blood cell MP (Healthy MP) or SCD red blood cell MP (SCD MP) at 25 MP/ml. After 1 hour, the ROS sensistive fluorescent probe DFF was added to the wells. After another 30 minutes, the accumulated fluorescence was analyzed in an automated plate reader. (*) p<0.05 versus control (none) ; (#) p<0.05 versus healthy RBC MP.

Figure 12:
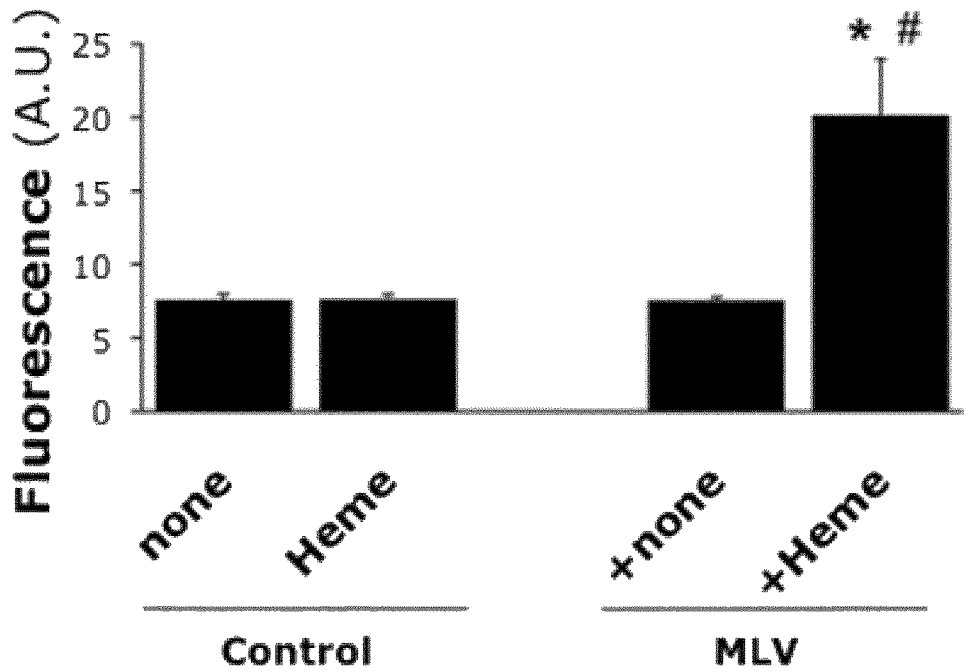

FIG. 12: Endothelium: Radical oxygen species generation in response to synthetic multimalar vesicles (MLV) artificially loaded in heme. Confluent HUVEC endothelial cells were incubated for 2 hours in the absence (none) or presence of synthetic multilamelar vesicles (MLV; at 25 MP/ml), alone or previously loaded in heme in vitro. After 1 hour, the ROS sensistive fluorescent probe DFF was added to the wells. After another 30 minutes, the accumulated fluorescence was analyzed in an automated plate reader. In some wells, HUVEC were incubated with heme in solution (5 uM), at a concentration at least equivalnt to that contained in the heme-loaded MLV. (*) p<0.05 versus 'none' (control) ; (#) p<0.05 versus MLV alone (+none).

Figure 13:
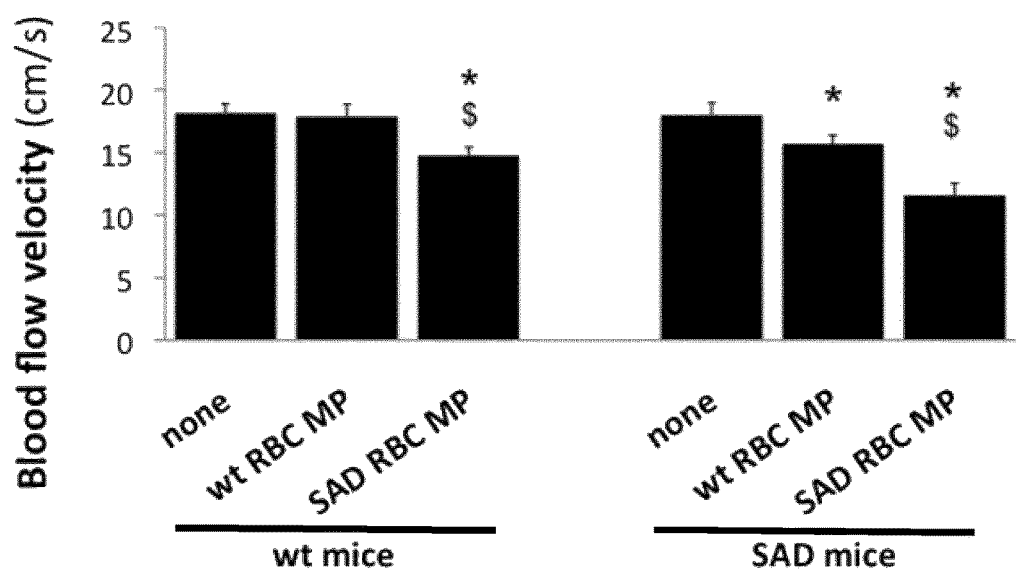

FIG. 13: Vaso-occlusive crises induced by red blood cell MP. Purified MP shed by wild type or transgenic SAD mouse RBC in vitro were injected intravenously to wild type (Green) or SAD (Pink) male mice, about 16 weeks of age, at the dose of 350×103 MP/mice. To determine the occurrence of a vaso-occlusive crisis, we measured the blood flow velocity in the right kidney artery by Echo-Doppler for 15 minutes after delivery of MP. (*) p<0.05 versus none (control at rest). ($) p<0.05 versus wt RBC MP.

EXAMPLE 1

Animals

We used 10-14 week old males of C57b16J background unless otherwise indicated. We bred male SAD transgenic mice obtained from Dr Beuzard (9) and carrying a human hemoglobin β chain transgene with 3 mutations (βS β$^6$Val, βS-Antilles β$^{23}$Ile and D-Punjab β$^{121}$Glu). Genotype was confirmed through electrophoretic characterization of blood hemoglobins at the hematology department of the Hôpital Européen George Pompidou in Paris. Wild type (wt) animals were control littermates from the above colonies, or procured through Charles River, France. All procedures for study animal care and euthanasia followed the European Community standards (authorization #00577). Protocols were validated by the local Inserm ethics committee.

Reagents

Human recombinant TSP1 was produced by EMP-Genetech (Germany). Synthetic peptides (17) 4N1-1 (RFYVVMWK) (SEQ ID NO:1) and 4N1-2 (RFYVVM) (SEQ ID NO:2) were obtained from Bachem, 4NGG (RFYGGMWK) (SEQ ID NO:3) is manufactured by Genecust (France). Di-aminodophenylindol (DAPI), RNase A, and propidium iodide were from Sigma-Aldrich.

Vaso-occlusive Crises in Mice

We characterized the induction of VOC in SAD transgenic mice (18, 19) according to our previously published method, in response to the intravenous administration of TSP1 (1 mg/kg), TSP1-derived peptides 4N1-1 or 4N1-2, or purified erythrocyte MP. Briefly, mice were anesthetized with isoflurane and monitored to prevent any cardiorespiratory depression. Mice were shaved and placed in the decubitus position on a heating blanket (38° C.). We used a Vivid 7 echograph (GE Medical Systems®, Horten, Norway) equipped with a 12-MHz linear transducer (12 L). The ultrasound probe was placed on the left side of the abdomen for examination of renal arteries, or in left lateral decubitus for cardiac output acquisition with transducer on the chest. Data were transferred on-line to an EchoPAC ultrasound image analysis workstation (GE Medical Systems®). Two-Dimensional ultrasound imaging of the abdomen in left-sided longitudinal B-mode allowed kidney width and height measurements. Color-coded blood flow detection by Doppler enabled renal arteries to be localized. A pulsed Doppler spectrum was recorded and peak systolic, end-diastolic and time-average mean BFV were measured in the renal artery, with Doppler beam angle correction. To calculate cardiac output, spatial flow profiles were analyzed in parasternal long-axis B-mode images of the pulmonary artery and BFV were measured as above. The following formula was applied: $CO=[(V^{mean} \cdot 60) \cdot (\pi \cdot (Dpa/2^2)]$, where CO is the cardiac output in ml/minute, $V^{mean}$ is the mean time-averaged BFV in cm/s and Dpa is the pulmonary artery diameter in cm. Kidney sizes and BFV were determined by the same investigator, as means of 5 to 8 measurements. Repeatability for cardiac output measurements was verified. We controlled and confirmed that kidney size was similar between SAD and wild type mice. After sacrifice, kidneys were dissected, dehydrated, mounted in paraffin, sectioned and stained by Masson trichrome. Vascular congestion was observed by phase-contrast microscopy, as large erythrocyte aggregates occluding kidney capillaries and larger vessels. In some experiments, TSP1 (1 mg/kg) or control BSA (1 mg/kg) were injected. After 5 minutes, mice were terminally anesthetized by pentobarbital overdose. Whole blood was collected through cardiac puncture, centrifuged (400 g, 15 minutes) to eliminate erythrocytes and leukocytes, and double centrifuged (12500 g, 5 minutes) to eliminate platelets with minimal activation. Supernatants were considered platelet-free plasma (PFP). Circulating MP were quantified by FACS.

Erythrocyte Suspensions

Mouse blood was obtained through retro-orbital sinus puncture, mixed with anti-coagulant heparin buffer (5 UI/ml), and collected on citrated tubes. Blood diluted 1:1 with PBS (Gibco-Life Sciences) was placed onto histopaque-1083 (Sigma) density gradients for centrifugation (600 g, 25 minutes). Erythrocyte pellets were resuspended, washed in DMEM and stored for up to 4 hours at room temperature. Erythrocyte surface CD47 expression was assessed by FACS. Fresh RBC were washed and blocked with PBS-BSA 5% for 30 min and immunoreacted with mouse-specific fluoroisothiocyanate (FITC)-coupled anti-CD47 monoclonal antibody (clone mIAP301; BD Biosciences, Le Pont de Claix, France), or matched irrelevant $IgG_{2a\kappa}$ isotype for 45 min in 2% PBS-BSA. Erythrocytes were washed in PBS-BSA 2% prior to FACS analysis. Erythrocyte phenotypes were analyzed by scanning electronic microscopy. Briefly, mouse erythrocytes were fixed with glutaraldehyde 1% and paraformaldehyde 4%, dehydrated and embedded in Epon™ epoxy resin. Sections contrasted with uranyl acetate and lead citrate were examined with a JEOL JEM 1010 microscope. Average apparent spicule number was determined by direct counting in 80 to 120 cells per condition.

MP Characterization

To trigger MP shedding, erythrocyte were suspended in polyvinylpyrrolidone (31 mPa.s) and placed in a rotating type LORCA ektacytometer (R&R Mechatronics, Hoorn, The Netherlands) in the absence or presence of TSP1 (25 μg/ml), or TSP1-derived peptides 4N1-1 or 4N1-2 (25 μM). Shear rate was applied according to the builder's program ($1500$ $s^{-1}$; 2.5 minutes). Erythrocytes were immediately separated and supernatant $PS^+$ MP quantified by FACS. Concentrated MP stocks were generated from 10 to 20 ml of supernatant from erythrocytes suspended in RPMI-1640 ($4.10^6$/ml) and treated with 4N1-1. Suspensions were centrifuged at 400 g for 15 min to discard cells, and ultracentrifuged at 20500 g for 45 min to pellet MP, which were resuspended in filtered (0.2 μm) DMEM and stored at −80° C. MP concentrations were determined as previously described (20). Briefly, MP were labeled with 2 μl FITC-conjugated annexin-V (Roche Diagnostics, France) diluted in 100 μl reaction buffer with 5 mM $CaCl_2$. $CaCl_2$ was omitted in negative controls. MP were analyzed on a Coulter EPICS XL flow cytometer (Beckman Coulter). MP were identified in forward light scatter (FSc) and side-angle light scatter (SSc) intensity dot plots set at logarithmic gain, as events of 0.1-1 μm in diameter. MP-size events were analyzed in FL/FSC fluorescence dot plots to determine annexin-V labeling. MP concentration was determined with respect to calibrated fluorescent microbeads (Flowcount). To determine erythrocyte origin, MP were double labeled with rat PE-Cy7-coupled mouse-specific anti-Ter119 antibody (Biolegend via Ozyme, France), or matched irrelevant $IgG_{2b\kappa}$ isotype.

Endothelial Cell Culture

SV40-transformed mouse lymph node endothelial cells (SVEC4-10 from ATCC) were obtained from LGC Promochem, France and grown in Dulbecco's Modified Eagle Medium (DMEM) supplemented with 20% neonatal calf serum (NCS ; Dominique Dutscher) in 24 well plaques at 37° C. with 5% $CO_2$. Confluent SVEC monolayers in 96 well plates were incubated with 25 MP/μl for up to 2 h. To determine ROS production, 5-(6-)Carboxy-2',7'-difluorodihydrofluorescein diacetate ($H_2DFF$-DA; 10 μM), was supplemented to the medium for the last 30 minutes, and fluorescence was read in an automated fluorescence plate reader. For erythrocyte adhesion experiments, MP-primed SVEC monolayers were washed and incubated with RBC suspensions in DMEM ($1.10^6$ RBC/ml). Supernatant cells were discarded after 30 min, and adherent cells were counted by phase contrast microscopy in 5 random fields per well (400×). All conditions were tested 3 to 6 times, in triplicates. In cell cycle analysis, SVEC were cultured up to 70% confluency, washed and placed in DMEM with 0.05% NCS with or without RBC MP. After 16 hours, SVEC were trypsinized, fixed overnight in ice-cold 70% ethanol-H20, and incubated in 0.05% Triton X100, 100 μg/ml RNase A plus 50 μg/ml propidium iodide for 1 h in the dark. Total DNA content was determined by FACS. DNA profiles were divided as sub-G1 (apoptosis), G0/G1 (resting) and G2/M (proliferation) phases of the cell cycle. Data shown is the mean percentage of cells in each phase, in 3 to 6 independent experiments.

Microvascular Dilation

Mesenteric arteries were removed from terminally anesthetized mice and placed them in ice-cold physiological salt solution (PSS). 4-6 arterial segments from each mouse were used. A segment of mesenteric artery was cannulated and mounted in a video-monitored perfusion system as described (21). Arterial segments were bathed in a 5 ml organ bath containing a PSS maintained at pH 7.4, with $pO_2$ and $pCO_2$ of 160 mm Hg and 37 mm Hg, respectively. Arterial diameter was continuously recorded by video (Living System Instrumentation Inc., Burlington, Vt.). Pressure and flow rates could be changed independently. Diameter changes were measured in each segment when the intraluminal pressure was set at 75 mm Hg in order to measure dilation. Artery viability was tested with potassium-rich solution (80 M; PSS). The endothelium was considered functional when 80% relaxation was obtained with $10^{-6}$ acetylcholine (ACH), after phenylephrine (PE)-induced preconstriction (50% of maximal contraction with KCl 80 mM). A cumulative concentration-response curve to ACH ($10^{-7}$-$10^{-4}$ M) was constructed after preconstriction. Sodium nitroprusside (SNP, 100 μM) was tested after the ACH curve. Intraluminal flow was then increased to 21 μl/minute and MP were injected in the vessel. A new cumulative concentration-response curve to ACH after was constructed after new PE-induced preconstriction. The experiment closed with a test with SNP (100 μM). At the end of each experiment, arteries were perfused and superfused with a $Ca^{2+}$-free PSS containing ethylenebis-(oxyethylenenitrolo) tetra-acetic acid (EDTA, 2 mM), SNP (10 μM)

and papaverine (10 Pressure (75 mm Hg) was then applied in order to determine passive diameters (i.e. without muscular tone). Pressure and diameter measurements were collected using a Biopac data acquisition system (Biopac MP 100, La Jolla, Calif., USA, and the Acqknowledge® software, Biopac).

Statistical Analysis

For in vivo VOC and ex vivo vasodilation experiments, inter-group comparisons (5-6 animals/group) were performed by variance analysis (One- or two-way ANOVA), completed by post hoc Bonferroni test, or/and paired or unpaired Student's t-tests (MedCalc software). In vitro experiments were repeated at least three times, and statistical analysis was performed with the unpaired student t-test. Results were expressed as mean±sem. Statistical significance was achieved when p value <0.05.

Results:

TSP1 Triggered Vaso-occlusive Crises in SAD Mice

We evaluated the concept that TSP1 influences VOC during SCD in vivo. We used SAD transgenic mice that express a mutated human hemoglobin β-chain known to cause sickle cell formation and sensitivity to VOC (18, 19). In SAD mice, VOC are not identified by the expression of pain as in humans, but on a reduction of perfusion in organs sensitive to vaso-occlusion, revealed by a drop in local mean blood flow velocities measured by Echo-Doppler.

Raising plasma TSP1 experimentally by intravenous injection (1 mg/kg) induced a rapid 20% reduction in the mean blood flow velocity of the right renal arteries of SAD mice, progressing to 35% after 5 minutes. Systolic, diastolic and mean blood flow velocities remained unchanged in wild type after TPS1 injection. In SAD mice, systolic blood flow velocity was unchanged after TSP1 injection, but diastolic and mean blood flow velocities were dramatically decreased. No changes occurred in cardiac output or heart rate. Renal histology after Masson trichrome stain revealed red blood cells aggregates and vascular congestion. TSP1 affected none of these parameters in wild type mice.

TSP1 Upregulated Plasma MP in vivo

After VOC experiments with TSP1 in SAD mice, we collected platelet-depleted plasma and quantified circulating $PS^+$ MP. TSP1 injections triggered a 3 fold raise in plasma $PS^+$ MP within 5 minutes in wild type mice (p<0.05 vs control). SAD mice displayed a doubling in circulating $PS^+$ MP levels at rest versus wild type mice (p<0.05). They also responded to TSP1 with a 3 fold increase in circulating $PS^+$ MP (p<0.05 vs control SAD and versus TSP1-treated wild type mice). Next, we injected a CD47 agonist, the TSP1 carboxyterminal peptide 4N1-1. Its effects were comparable to whole TSP1. We also show that fresh wild type and SAD RBC display similar levels of CD47 expression (85%) by FACS.

TSP1 Induced RBC Conversion into Echinocytes and MP Shedding

We asked whether TSP1 could mediate significant modifications in isolated erythrocyte phenotype, or in MP shedding. Fresh wild type and SAD mouse erythrocytes were placed under shear in a Lorca ektacytometer. Phase contrast and electron microscopic analysis revealed that echinocytes were rather rare in healthy wild type RBC. However, the addition of TSP1 raised the proportion of wild type echinocytes over 10 fold to reach 30% within minutes (p<0.05 vs control). The pattern of short spicules of the healthy echinocytes was predictable by surface tension analysis (22, 23). In contrast, SAD erythrocytes at rest displayed a great variety of shapes with elongated deformed bodies, including about 5% of typical sickle erythrocytes. TSP1 triggered a 50% increase in SAD echinocytes (p<0.05 vs control), but did not affect sickle cells. Conversion into SAD echinocytes was accompanied by $PS^+$ MP shedding (p<0.05).

Next, we evaluated the effects of TSP1 carboxyterminal peptides including the CD47 agonist 4N1-1, truncated control 4N1-2, and mutated control 4NGG devoid of the original VVM motif 4N1-1 proved particularly strong stimulus of echinocytosis with a doubling in wild type echinocytes and a 50% increase in SAD echinocytes (p<0.05), similar to recombinant TSP1. 4N1-1 did not affect sickle cells. 4N1-1 also triggered intense MP shedding with a 16 fold increase in wild type erythrocytes and a 40 fold raise in SAD erythrocytes (p<0.05 versus control peptides), whereas 4N1-2 and 4NGG had no effect. Again, SAD RBC shed about twice as many MP than healthy erythrocytes whether stimulated or at rest, and more particularly when TSP1 or 4N1-1 are applied (p<0.05 wild type vs SAD). Scanning electron microscopy of SAD erythrocytes revealed that echinocytosis occurred as a drastic phenotypic change with the multiplication of unusually thin, long and apparently fragile spicules, as shown after treatment with 4N1-1. In contrast spicule dimensions appeared strikingly homogenous in wild type cells. Interestingly, 4N1-1 increased spicule numbers in SAD RBC by 20% (p<0.05 vs wild type) and not in healthy wild type erythrocytes.

Erythrocyte MP Mediated Vaso-occlusive Crises in SAD Mice

We purified MP derived from wild type or SAD RBC treated in vitro with 4N1-1 peptide. We studied their impact on the occurrence of VOC in SAD mice. We administered MP intravenously at a concentration selected on the basis of our measurements in healthy mice (400 MP/µl), and the known circulating levels in humans (400-1000 MP/µl) (6, 24). Steady state SCD patients were previously shown to display circulating levels of $PS^+$ MP that are 3 to 6 fold higher than health, particularly those of erythrocyte origin (4-6, 8, 24). We confirmed similar observations in SAD mice (about 1000 MP/ml). Furthermore, $PS^+$ MP levels in patients are known to increase 0.5 to 3 fold further during VOC versus steady state (7, 8, 25). We injected mice with $300.10^3$ MP/mouse (about 100 MP/µl), for an increase equivalent to ¼ of wild type circulating levels.

SAD RBC MP induced a 30 to 35% reduction in mean blood flow velocity in SAD mice renal arteries (FIG. 1A; p<0.05 vs none). In SAD mice, systolic blood flow velocity was unchanged after MP injection, but diastolic and mean blood flow velocities were dramatically decreased. No changes occurred in cardiac output or heart rate. At this concentration, wild type RBC MP had very similar effects (p<0.05 vs controls). Renal histology after Masson trichrome stain revealed red blood cells aggregates and vascular congestion in SAD mice.

In other experiments, we pre-incubated the purified SAD RBC MP with annexin-V to saturate the PS at their surface and washed them. We injected the annexin-V-saturated MP to SAD mice ($300.10^3$ MP/mouse), and they failed to modify VOC parameters, (p<0.05 vs untreated SAD RBC MP).

Erythrocyte MP Activate Endothelial Cells

In an attempt to elucidate the mechanisms that link circulating RBC MP to VOC, we pursued investigations in endothelial cells. We cultured murine endothelial monolayers in 0.2 µm-filtered medium, with addition of wild type or SAD RBC MP (25 MP/µl) for up to 18 hours. We chose to analyze several key parameters thought to influence VOC, comprising ROS production, RBC adhesion and apoptosis.

Fresh wild type RBC MP stimulated little endothelial ROS production over basal levels detected by $H_2DFF-DA$ assay in 2 hours (+10%; p<0.05). In contrast, SAD RBC MP at the same concentration more than doubled endothelial ROS generation (p<0.05 vs wild type MP). ROS generation induced by SAD RBC MP was entirely inhibited when the MP PS was previously saturated with recombinant annexin-V (1 µg/ml for 1 hour). ROS generation was also prevented when endothelial NADPH oxydase was blocked by incubation with 10 µM DPI or 100 µM apocynin for 30 minutes, or when endothelial PKC activity was inhibited with 1 µM Ro-31-8220 or 1 µM Gö-6976 (p<0.05 vs MP alone). Alternatively, ROS generation induced by SAD RBC MP was entirely inhibited when endothelial NOS was blocked with 100 µM L-NAME, whereas its enantiomer D-NAME had no effects (p<0.05).

Next, we studied erythrocyte adhesion to MP-primed confluent endothelial monolayers. Healthy wild type erythrocytes showed little affinity for endothelium, no matter how it was pre-incubated (under 5 cells/field). On the other hand, SAD erythrocytes adhered to endothelium at least twice more than wild type cells, even without pretreatment (p<0.05). Priming endothelium with wild type erythrocyte MP (25 MP/µl for 2 hours) barely had any effects on wild type erythrocyte adhesion, and had modest effects on SAD erythrocyte adhesion (+20%; p<0.05). However, endothelial priming with SAD erythrocyte MP strongly increased SAD RBC adhesion about 3 fold (p<0.05 vs control).

In other experiments, we left wild type erythrocyte MP on endothelial monolayers for 16 hours in the presence of reduced NCS (0.05%). MP from wild type erythrocytes had no effects on cell cycling, neither on proliferation (G2/M phase), nor apoptosis (Sub-G1 fraction). However, SAD MP doubled endothelial apoptosis versus wild type MP (p<0.05).

We wanted to demonstrate the impact of RBC MP on endothelial function and vasodilation. Resistance arteries were perfused with PSS in a pressure myograph (75 mm Hg intraluminal pressure; 21 µl/min flow). Arteries were pre-constricted with phenylephine and we assessed vasodilation in response to increasing doses of ACH ($10^{-7}$ M to $10^{-4}$ M). Next, arteries were washed and pre-constricted again. Then, SAD or wild type RBC MP were perfused and vasodilation was measured in response to increasing ACH concentrations. We found that RBC MP strongly reduced the sensitivity of resistance arteries to ACH-mediated vasodilation. But SAD RBC MP blocked vasodilation even further than wild type RBC MP (p<0.05).

As control, for smooth muscle integrity, we evaluated vasodilation in response to the NO donor SNP. We found no impact of PE and ACH treatments on subsequent SNP-induced vasodilation, consistent with functional vascular smooth muscle (vessel diameter 90±3% of maximal vessel diameter). In contrast, exposure to wild type or SAD RBC MP reduced SNP vasodilation down to 69±5% and 59±6% of maximal vessel diameter, respectively (p<0.05 vs control). This suggested some vascular smooth muscle injury. However, two thirds of impact of RBC MP on vasodilation could be attributed to endothelial injury.

Figure 4A:
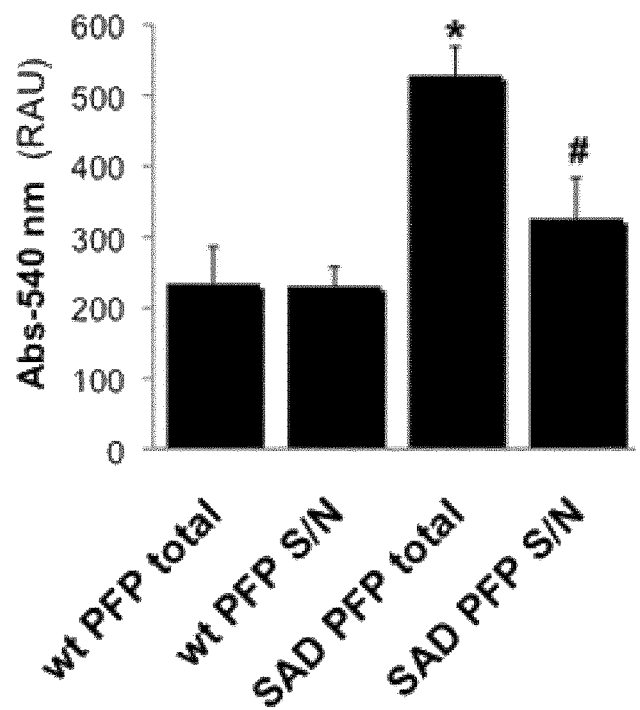
Figure 4B:
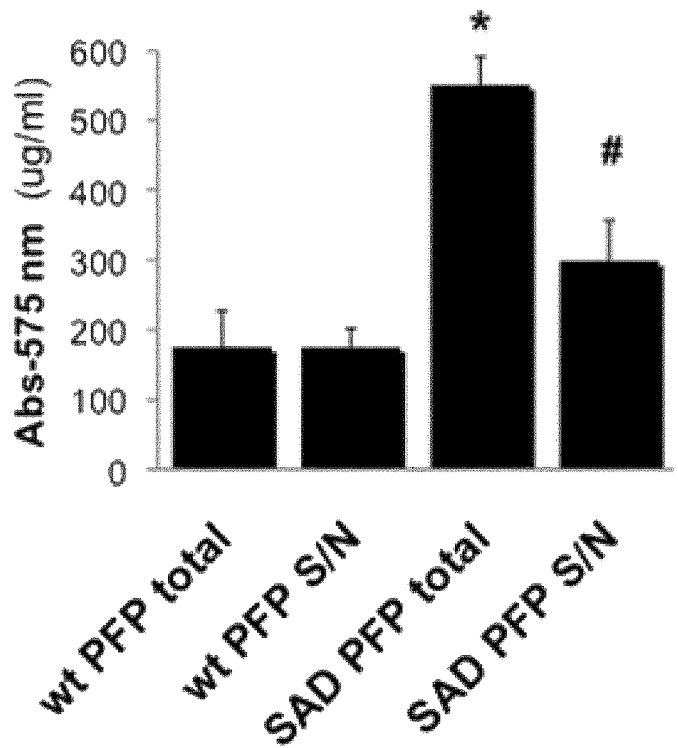
Figure 4C:
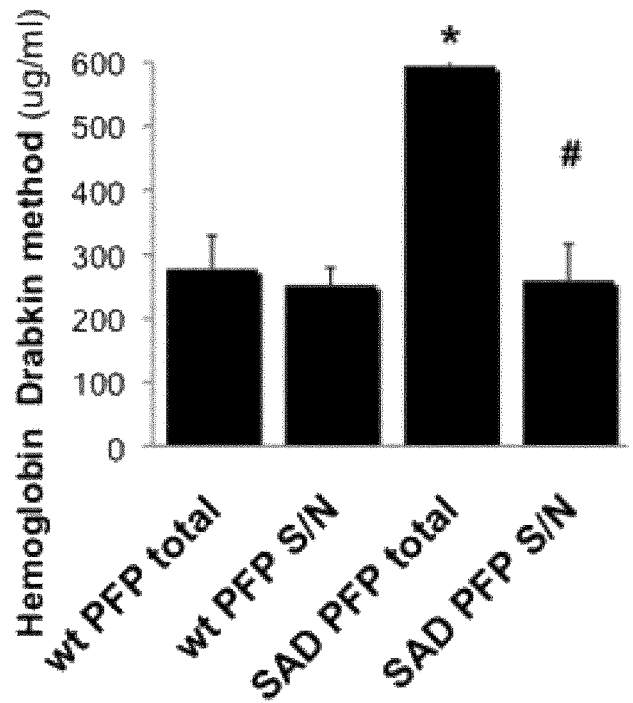
Figure 4D:
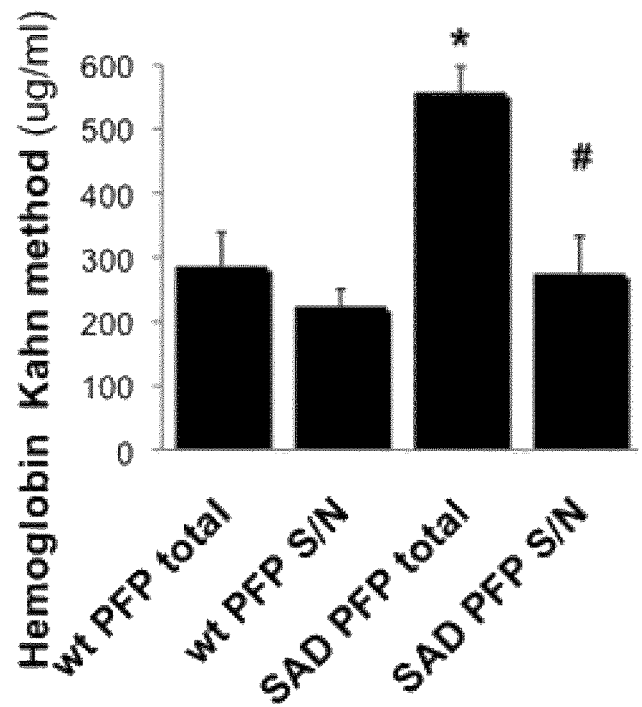
Figure 4E:
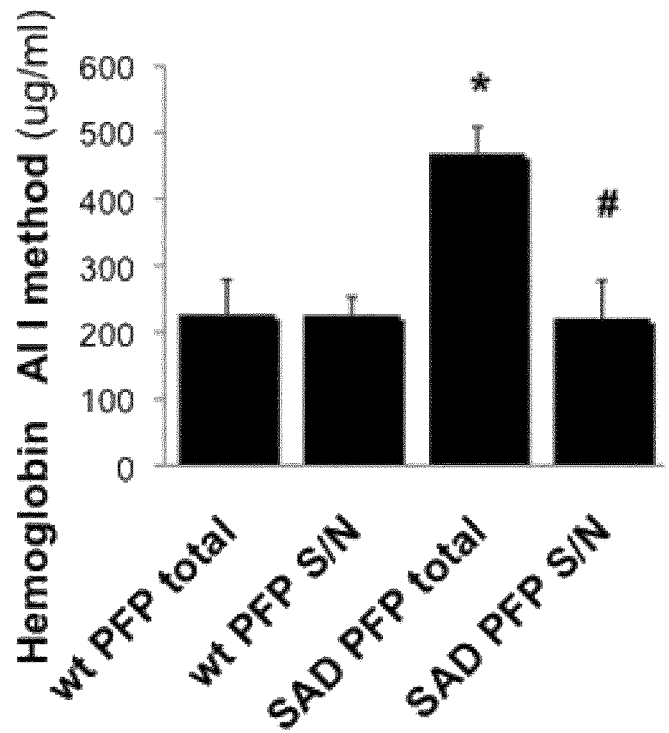
Figure 4F:
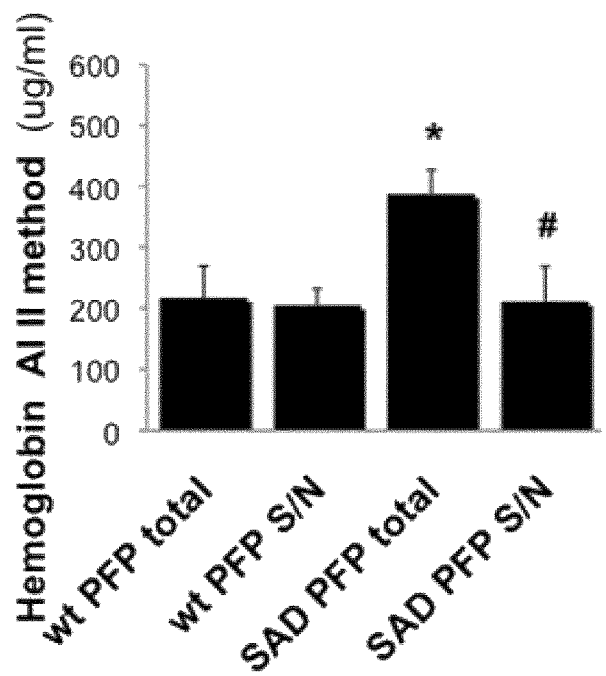

Pre-incubating MP with recombinant annexin-V (1 µg/ml; 1 hour), or treating the vessel with the superoxide dismutase mimetic Tempol (10 µM; 30 minutes) reduced the deleterious effects of SAD RBC MP (−20% and −50% respectively; p<0.05 vs MP alone), and preserved some ACH-mediated vasodilation (FIG. 4H). Tempol alone had little effects (−5% vessel diameter, p<0.05 vs control).

Discussion:

Circulating MP have long been reported as a key feature of SCD in conjunction with hemolysis. However, the mechanisms of their generation and their physiopathological impact remained unknown.

TSP1 Triggers Vaso-occlusive Crises

TSP1 is mainly stored in platelets and released upon activation to generate steep and local gradients. TSP1 can also be secreted by vascular cells challenged with thrombin (26), hypoxia (27, 28), mechanical injury (29), or abnormal blood flow (30-32). With platelet counts of $250.10^6$ platelets/ml and 80 ng TSP1 per $10^6$ platelets, 1 ml of normal human blood contains over 20 µg TSP1 (10). Coagulated human blood contains 17.5 µg/ml of TSP1 (33). Moreover, basal systemic plasma TSP1 concentrations are similar in health and steady state SCD patients (about 0.5 µg/ml). However, TSP1 increases sharply during VOC (up to 5 fold) (10). In healthy wild type mice, Hoylaerts and colleagues reported basal circulating TSP1 levels of 1.8 µg/ml (34). Hence, we selected intravenous injections of 1 mg/Kg TSP1 (about 10 ug/ml) to mimic a maximal 5 fold systemic increase to investigate the links between TSP1, MP and VOC in vivo.

In SAD mice, TSP1 injection induced a 30% drop in renal perfusion within minutes, but TSP1 had no impact on systemic hemodynamic parameters such as cardiac output or heart rate. The drop in SAD renal perfusion is thus consistent with a local increase in renal vascular resistance and related to VOC (18, 19). This was confirmed by histological assessment of severe renal capillary congestion and obvious signs of pain in injected SAD mice, including temporary prostration and reduced mobility after the end of anesthesia. Unexpectedly, TSP1 did not modify renal perfusion in wild type mice. The deleterious effects of TSP1 were only revealed in transgenic SAD mice, in territories susceptible to vaso-occlusion. At rest, SAD PFP contained twice as many MP than wild type PFP (880 vs. 400 MP/µl, respectively). We observed a 3 fold increase in plasma MP in both wild type and SAD animals within 5 minutes of TSP1 injection. Hence, MP shedding coincided with VOC in SAD mice. Since VOC are associated with drastic erythrocyte remodeling, we wondered whether plasma TSP1 could trigger any of the erythrocyte modifications observed during VOC in humans.

TSP1 Signals Conversion into Echinocytes and MP Shedding

We worked with fresh purified wild type and SAD mouse erythrocytes in vitro. To reproduce physiological hemorheological parameters, we placed erythrocytes in dynamic conditions matching the shear rates present in veins. Phase contrast and electron microscopy revealed that TSP1 induced wild type erythrocyte crenation, producing condensed echinocytes covered in cone-shaped membrane spicules (1, 3). Conversion into echinocytes and back to discocytes is a reversible process in healthy RBC. However, repeated cycles are thought to gradually deteriorate erythrocytes expressing HbS, producing deformed, stiff and adherent cells. Circulating echinocytes exist in SCD patients at steady state, but they are particularly present during VOC (2). However, functional significance remains unclear. In wild type erythrocytes in vitro, the conversion into echinocytes occured within 2 minutes of TSP1 stimulation, producing a predictable pattern of short spicules (22, 23), similar to those reported for the $Ca^{2+}$ ionophore A23187 (35) or ATP depletion (3). In wild type RBC, echinocyte conversion correlated with PS externalization and $PS^+$ MP shedding. This is coherent with previous reports on the induction of erythrocyte PS externalization by TSP1 (36), on the correlation of PS externalization with spicule formation (35, 37), and on the suggested role of spicules in vesiculation (1, 38).

Transgenic SAD erythrocytes at rest displayed a great variety of elongated and deformed shapes. True sickle cells represented less than 5% of SAD erythrocytes, whereas echinocytes accounted for up to 30%. TSP1 and shear stress induced PS externalization, doubled the proportion of SAD echinocytes (p<0.05 vs control) and doubled MP shedding (p<0.05 vs control). SAD echinocytes displayed highly unpredictable phenotypes and a heterogeneous number of thin and long spicules. Moreover, SAD echinocytes shed twice more MP than healthy cells with TSP1. MP shedding correlated with the proportion of echinocytes, and the numbers and putative fragility of SAD spicules might also participate in greater MP shedding.

Carboxyterminal Peptides Reproduce the Stimulation of MP Shedding by TSP1 In erythrocytes and reticulocytes, highly conserved VVM sequences in the TSP1 carboxyterminus are thought to play a key role in activating CD47 receptors (39-42). CD47, also known as integrin-associated protein (IAP) in platelets and leukocytes, is a key constituent of the Rhesus protein complex. CD47 activation is known to enhance integrin avidity and recapitulate the pro-adhesive effects of TSP1 on sickle erythrocytes (13-16). Synthetic peptides including 4N1-1 (17) mimic these carboxyterminal sequences and reproduce some of the functions of TSP1, although the peptides may have additional effects (39-42).

Here, the vast majority of wild type and SAD erythrocytes expressed cell surface CD47. Like TSP1, 4N1-1 peptide triggered PS externalization, echinocyte conversion and MP shedding, in vitro and in vivo, whereas truncated or mutated peptides did not, coherent with CD47 activation. TSP1-CD47 signaling was previously reported to include rapid cytosolic $Ca^{2+}$ mobilization (43), cytoskeletal remodeling (44, 45) and membrane PS externalization (36, 45, 46) in fibroblasts and lymphocytes. CD47 may thus mediate the mechanical properties of the RBC membrane and trigger vesiculation.

One singular difference between TSP1 and 4N1-1 is that the presence of shear stress was necessary to unmask the effects of TSP1, whereas 4N1-1 remained active at rest. Shear might thus synergize with the TSP1 carboxyterminus to activate CD47. Indeed, CD47 has already been proposed as a mechanosensor, and CD47 signaling is strongly enhanced by shear in SCD erythrocytes (15). However, the nature of this synergy is still not understood, dedicated molecular studies will be needed to determine how shear influences CD47 activation by TSP1.

Erythrocyte MP Trigger Vaso-occlusive Crises

We investigated the impact of SAD and wild type erythrocyte MP on VOC in mice. After inducing erythrocyte vesiculation in vitro with 4N1-1, we concentrated purified the MP and administered them to produce a 20% increase in plasma versus steady state. SAD MP triggered a rapid and drastic reduction in renal perfusion in SAD mice. We noted a tendency to a slight reduction in heart rates with SAD MP over time. However, this did not materialize in a reduction in cardiac output. Furthermore, the slowing of heart rate (up to −10%) remained insufficient to explain the reductions in blood flow velocity observed in kidneys (up to −35%). Histological analysis confirmed the induction of renal capillary congestion and we concluded that SAD MP induced severe VOC. Unexpectedly, the effects of healthy MP were similar to SAD MP and induced VOC at this concentration. This contrasted with in vitro results showing enhanced effects of SAD MP of vascular endothelium. It is possible that the injected healthy MP numbers, although conservative (raising blood MP by about 25%), exceeded the thresholds necessary to induce VOC, precluding finer distinctions. Nevertheless, erythrocyte MP were sufficient to trigger VOC and may represent secondary mediators of TSP1 in SCD.

Erythrocyte MP Activate the Endothelium

To determine how erythrocyte MP might induce VOC, we investigated their impact on cultured endothelium and isolated microvessels. Fresh wild type erythrocyte MP barely increased endothelial ROS production in culture, but SAD erythrocyte MP doubled endothelial ROS generation within 2 hours. This ROS production was sensitive to both NADPH oxidase and NOS inhibitors, suggesting that RBC MP may activate NADPH oxidase and generate excess superoxide. This superoxide may react with endothelial nitric oxide to form highly cytotoxic peroxynitrite. We used $H_2DFF-DA$ to detect ROS in vitro, a probe sensitive to peroxynitrite.

In live resistance arteries, perfused erythrocyte MP greatly reduced ACH-mediated endothelial-dependent vasodilation. SAD MP were more deleterious than wild type MP, coherent with the increased ROS stimulation in cultured endothelium. The effects of MP on endothelial function were mediated ROS and the phosphatidylserine carried at the MP surface. These data and the neutralizing effects of the superoxide dismutase mimetic Tempol was coherent with the proposed sequestration of NO into peroxynitrites and endothelial function.

Endothelial incubation with MP also increased the adhesion of erythrocytes. At rest, SAD erythrocytes are twice more adherent than wild type erythrocytes. Priming the endothelium with SAD RBC MP for 2 hours resulted in a 3 fold rise in subsequent SAD erythrocyte adhesion, but had little effects with wild type erythrocytes. SAD MP may thus synergize with intrinsic SAD erythrocyte features to maximize their adhesion. Endothelial activation by erythrocyte MP may represent a critical step in the initiation of vaso-occlusions. In the long term, SAD erythrocyte MP left on endothelial monolayers for 16 hours induced significant apoptosis, whereas wild type MP did not.

RBC MP may be able to enhance several processes thought to be critical to VOC induction, namely endothelial damage, RBC adhesion and impaired vasodilation. These effects may also contribute to the progression of vasculopathy and the degenerative manifestations associated with sickle cell disease. ROS production and impaired endothelial function could be prevented by saturating PS with recombinant annexin-V. Annexin-V also abrogated the induction of VOC by RBC MP in vivo, suggesting that PS is a key functional feature of circulating MP and may open novel therapeutic possibilities to treat VOC. Further experiments will be necessary to determine the importance of this pathway in human SCD.

REFERENCES

Throughout this application, various references describe the state of the art to which this invention pertains. The disclosures of these references are hereby incorporated by reference into the present disclosure.

1. Allan, D., Limbrick, A. R., Thomas, P., and Westerman, M. P. 1982. Release of spectrin-free spicules on reoxygenation of sickled erythrocytes. Nature 295:612-613.
2. Warth, J. A., and Rucknagel, D. L. 1984. Density ultracentrifugation of sickle cells during and after pain crisis: increased dense echinocytes in crisis. Blood 64:507-515.

3. Chabanel, A., Reinhart, W., and Chien, S. 1987. Increased resistance to membrane deformation of shape-transformed human red blood cells. Blood 69:739-743.

4. Wun, T., Paglieroni, T., Tablin, F., Welborn, J., Nelson, K., and Cheung, A. 1997. Platelet activation and platelet-erythrocyte aggregates in patients with sickle cell anemia. J Lab Clin Med 129:507-516.

5. Setty, B. N., Kulkarni, S., Rao, A. K., and Stuart, M. J. 2000. Fetal hemoglobin in sickle cell disease: relationship to erythrocyte phosphatidylserine exposure and coagulation activation. Blood 96:1119-1124.

6. Westerman, M., Pizzey, A., Hirschman, J., Cerino, M., Weil-Weiner, Y., Ramotar, P., Eze, A., Lawrie, A., Purdy, G., Mackie, I., et al. 2008. Microvesicles in haemoglobinopathies offer insights into mechanisms of hypercoagulability, haemolysis and the effects of therapy. Br J Haematol 142:126-135.

7. Shet, A. S., Aras, O., Gupta, K., Hass, M. J., Rausch, D. J., Saba, N., Koopmeiners, L., Key, N. S., and Hebbel, R. P. 2003. Sickle blood contains tissue factor-positive microparticles derived from endothelial cells and monocytes. Blood 102:2678-2683.

8. van Beers, E. J., Schaap, M. C., Berckmans, R. J., Nieuwland, R., Sturk, A., van Doormaal, F. F., Meijers, J. C., and Biemond, B. J. 2009. Circulating erythrocyte-derived microparticles are associated with coagulation activation in sickle cell disease. Haematologica 94:1513-1519.

9. Trudel, M., Saadane, N., Garel, M. C., Bardakdjian-Michau, J., Blouquit, Y., Guerquin-Kern, J. L., Rouyer-Fessard, P., Vidaud, D., Pachnis, A., Romeo, P. H., et al. 1991. Towards a transgenic mouse model of sickle cell disease: hemoglobin SAD. EMBO J 10:3157-3165.

10. Browne, P. V., Mosher, D. F., Steinberg, M. H., and Hebbel, R. P. 1996. Disturbance of plasma and platelet thrombospondin levels in sickle cell disease. Am J Hematol 51:296-301.

11. Beurling-Harbury, C., and Schade, S. G. 1989. Platelet activation during pain crisis in sickle cell anemia patients. Am J Hematol 31:237-241.

12. Bonnefoy, A., Daenens, K., Feys, H. B., De Vos, R., Vandervoort, P., Vermylen, J., Lawler, J., and Hoylaerts, M. F. 2006. Thrombospondin-1 controls vascular platelet recruitment and thrombus adherence in mice by protecting (sub)endothelial VWF from cleavage by ADAMTS13. Blood 107:955-964.

13. Brittain, H. A., Eckman, J. R., Swerlick, R. A., Howard, R. J., and Wick, T. M. 1993. Thrombospondin from activated platelets promotes sickle erythrocyte adherence to human microvascular endothelium under physiologic flow: a potential role for platelet activation in sickle cell vaso-occlusion. Blood 81:2137-2143.

14. Brittain, J. E., Mlinar, K. J., Anderson, C. S., Orringer, E. P., and Parise, L. V. 2001. Integrin-associated protein is an adhesion receptor on sickle red blood cells for immobilized thrombospondin. Blood 97:2159-2164.

15. Brittain, J. E., Mlinar, K. J., Anderson, C. S., Orringer, E. P., and Parise, L. V. 2001. Activation of sickle red blood cell adhesion via integrin-associated protein/CD47-induced signal transduction. J Clin Invest 107:1555-1562.

16. Brittain, J. E., Han, J., Ataga, K. I., Orringer, E. P., and Parise, L. V. 2004. Mechanism of CD47-induced alpha4beta1 integrin activation and adhesion in sickle reticulocytes. J Biol Chem 279:42393-42402.

17. Kosfeld, M. D., and Frazier, W. A. 1993. Identification of a new cell adhesion motif in two homologous peptides of the COOH-terminal cell binding domain of human thrombospondin. J Biol Chem 268:8808-8814.

18. Bonnin, P., Sabaa, N., Flamant, M., Debbabi, H., and Tharaux, P. L. 2008. Ultrasound imaging of renal vaso-occlusive events in transgenic sickle mice exposed to hypoxic stress. Ultrasound Med Biol 34:1076-1084.

19. Sabaa, N., de Franceschi, L., Bonnin, P., Castier, Y., Malpeli, G., Debbabi, H., Galaup, A., Maier-Redelsperger, M., Vandermeersch, S., Scarpa, A., et al. 2008. Endothelin receptor antagonism prevents hypoxia-induced mortality and morbidity in a mouse model of sickle-cell disease. J Clin Invest 118:1924-1933.

20. Leroyer, A. S., Ebrahimian, T. G., Cochain, C., Recalde, A., Blanc-Brude, O., Mees, B., Vilar, J., Tedgui, A., Levy, B. I., Chimini, G., et al. 2009. Microparticles from ischemic muscle promotes postnatal vasculogenesis. Circulation 119:2808-2817.

21. Loufrani, L., Levy, B. I., and Henrion, D. 2002. Defect in microvascular adaptation to chronic changes in blood flow in mice lacking the gene encoding for dystrophin. Circ Res 91:1183-1189.

22. Lim, H. W. G., Wortis, M., and Mukhopadhyay, R. 2002. Stomatocyte-discocyte-echinocyte sequence of the human red blood cell: evidence for the bilayer-couple hypothesis from membrane mechanics. Proc Natl Acad Sci U S A 99:16766-16769.

23. Mukhopadhyay, R., Lim, H. W. G., and Wortis, M. 2002. Echinocyte shapes: bending, stretching, and shear determine spicule shape and spacing. Biophys J 82:1756-1772.

24. Mahfoudhi, E., Lecluse, Y., Driss, F., Abbes, S., Flaujac, C., and Garcon, L. 2011. Red cells exchanges in sickle cells disease lead to a selective reduction of erythrocytes-derived blood microparticles. Br J Haematol.

25. van Tits, L. J., van Heerde, W. L., Landburg, P. P., Boderie, M. J., Muskiet, F. A., Jacobs, N., Duits, A. J., and Schnog, J. B. 2009. Plasma annexin A5 and microparticle phosphatidylserine levels are elevated in sickle cell disease and increase further during painful crisis. Biochem Biophys Res Commun 390:161-164.

26. McLaughlin, J. N., Mazzoni, M. R., Cleator, J. H., Earls, L., Perdigoto, A. L., Brooks, J. D., Muldowney, J. A., 3rd, Vaughan, D. E., and Hamm, H. E. 2005. Thrombin modulates the expression of a set of genes including thrombospondin-1 in human microvascular endothelial cells. J Biol Chem 280:22172-22180.

27. Phelan, M. W., Forman, L. W., Perrine, S. P., and Faller, D. V. 1998. Hypoxia increases thrombospondin-1 transcript and protein in cultured endothelial cells. J Lab Clin Med 132:519-529.

28. Frangogiannis, N. G., Ren, G., Dewald, O., Zymek, P., Haudek, S., Koerting, A., Winkelmann, K., Michael, L. H., Lawler, J., and Entman, M. L. 2005. Critical role of endogenous thrombospondin-1 in preventing expansion of healing myocardial infarcts. Circulation 111:2935-2942.

29. Sajid, M., Hu, Z., Guo, H., Li, H., and Stouffer, G. A. 2001. Vascular expression of integrin-associated protein and thrombospondin increase after mechanical injury. J Investig Med 49:398-406.

30. McPherson, J., Sage, H., and Bornstein, P. 1981. Isolation and characterization of a glycoprotein secreted by aortic endothelial cells in culture. Apparent identity with platelet thrombospondin. J Biol Chem 256:11330-11336.

31. Freyberg, M. A., Kaiser, D., Graf, R., Buttenbender, J., and Friedl, P. 2001. Proatherogenic flow conditions initiate endothelial apoptosis via thrombospondin-1 and the integrin-associated protein. Biochem Biophys Res Commun 286:141-149.

32. Moura, R., Tjwa, M., Vandervoort, P., Cludts, K., and Hoylaerts, M. F. 2007. Thrombospondin-1 activates medial smooth muscle cells and triggers neointima formation upon mouse carotid artery ligation. Arterioscler Thromb Vasc Biol 27:2163-2169.

33. Dawes, J., Clemetson, K. J., Gogstad, G. O., McGregor, J., Clezardin, P., Prowse, C. V., and Pepper, D. S. 1983. A radioimmunoassay for thrombospondin, used in a comparative study of thrombospondin, beta-thromboglobulin and platelet factor 4 in healthy volunteers. Thromb Res 29:569-581.

34. Bonnefoy, A., Moura, R., and Hoylaerts, M. F. 2008. The evolving role of thrombospondin-1 in hemostasis and vascular biology. Cell Mol Life Sci 65:713-727.

35. Bratosin, D., Estaquier, J., Petit, F., Arnoult, D., Quatannens, B., Tissier, J. P., Slomianny, C., Sartiaux, C., Alonso, C., Huart, J. J., et al. 2001. Programmed cell death in mature erythrocytes: a model for investigating death effector pathways operating in the absence of mitochondria. Cell Death Differ 8:1143-1156.

36. Head, D. J., Lee, Z. E., Swallah, M. M., and Avent, N. D. 2005. Ligation of CD47 mediates phosphatidylserine expression on erythrocytes and a concomitant loss of viability in vitro. Br J Haematol 130:788-790.

37. Sakthivel, R., Farooq, S. M., Kalaiselvi, P., and Varalakshmi, P. 2007. Investigation on the early events of apoptosis in senescent erythrocytes with special emphasis on intracellular free calcium and loss of phospholipid asymmetry in chronic renal failure. Clin Chim Acta 382:1-7.

38. Iglic, A., Veranic, P., Jezernik, K., Fosnaric, M., Kamin, B., Hagerstrand, H., and Kralj-Iglic, V. 2004. Spherocyte shape transformation and release of tubular nanovesicles in human erythrocytes. Bioelectrochemistry 62:159-161.

39. Gao, A. G., Lindberg, F. P., Finn, M. B., Blystone, S. D., Brown, E. J., and Frazier, W. A. 1996. Integrin-associated protein is a receptor for the C-terminal domain of thrombospondin. J Biol Chem 271:21-24.

40. McDonald, J. F., Dimitry, J. M., and Frazier, W. A. 2003. An amyloid-like C-terminal domain of thrombospondin-1 displays CD47 agonist activity requiring both VVM motifs. Biochemistry 42:10001-10011.

41. Isenberg, J. S., Ridnour, L. A., Dimitry, J., Frazier, W. A., Wink, D. A., and Roberts, D. D. 2006. CD47 is necessary for inhibition of nitric oxide-stimulated vascular cell responses by thrombospondin-1. J Biol Chem 281:26069-26080.

42. Floquet, N., Dedieu, S., Martiny, L., Dauchez, M., and Perahia, D. 2008. Human thrombospondin's (TSP-1) C-terminal domain opens to interact with the CD-47 receptor: a molecular modeling study. Arch Biochem Biophys 478:103-109.

43. Schwartz, M. A., Brown, E. J., and Fazeli, B. 1993. A 50-kDa integrin-associated protein is required for integrin-regulated calcium entry in endothelial cells. J Biol Chem 268:19931-19934.

44. Tsao, P. W., and Mousa, S. A. 1995. Thrombospondin mediates calcium mobilization in fibroblasts via its Arg-Gly-Asp and carboxyl-terminal domains. J Biol Chem 270: 23747-23753.

45. Mateo, V., Brown, E. J., Biron, G., Rubio, M., Fischer, A., Deist, F. L., and Sarfati, M. 2002. Mechanisms of CD47-induced caspase-independent cell death in normal and leukemic cells: link between phosphatidylserine exposure and cytoskeleton organization. Blood 100:2882-2890.

46. Roue, G., Bitton, N., Yuste, V. J., Montange, T., Rubio, M., Dessauge, F., Delettre, C., Merle-Beral, H., Sarfati, M., and Susin, S. A. 2003. Mitochondrial dysfunction in CD47-mediated caspase-independent cell death: ROS production in the absence of cytochrome c and AIF release. Biochimie 85:741-746.

The invention claimed is:

1. A method for preventing or treating a vaso-occlusive crisis in a patient suffering from sickle cell disease comprising the step of administering to said patient a non-modified annexin V.

2. The method according to claim 1, wherein said patient is characterized by an increase of:
   (i) the level of cell microparticles in a blood sample; and/or
   (ii) the level of heme and/or hemoglobin contained in said cell microparticles.

3. The method according to claim 1, for preventing a vaso-occlusive crisis in a patient suffering from sickle cell disease.

4. The method according to claim 1, for treating a vaso-occlusive crisis in a patient suffering from sickle cell disease.

* * * * *

UNITED STATES PATENT AND TRADEMARK OFFICE
CERTIFICATE OF CORRECTION

PATENT NO. : 10,139,420 B2  
APPLICATION NO. : 14/003919  
DATED : November 27, 2018  
INVENTOR(S) : O Blanc-Brude et al.

Page 1 of 1

It is certified that error appears in the above-identified patent and that said Letters Patent is hereby corrected as shown below:

On the Title Page

Item (73) Please correct the second assignee's name to read "INSERM (Institut National de la Sante et de la Recherche Medicale)"

Signed and Sealed this
Eighteenth Day of February, 2020

Andrei Iancu
*Director of the United States Patent and Trademark Office*